(12) United States Patent
Badik et al.

(10) Patent No.: US 12,128,007 B2
(45) Date of Patent: Oct. 29, 2024

(54) SMART DISPENSER

(71) Applicant: KURE, LLC, Newark, DE (US)

(72) Inventors: Yale Badik, Madison, CT (US);
Deanna Felker, West Hills, CA (US)

(73) Assignee: KURE, LLC, Newark, NJ (US)

( * ) Notice: Subject to any disclaimer, the term of this patent is extended or adjusted under 35 U.S.C. 154(b) by 0 days.

(21) Appl. No.: 18/467,884

(22) Filed: Sep. 15, 2023

(65) Prior Publication Data

US 2024/0000665 A1   Jan. 4, 2024

Related U.S. Application Data

(63) Continuation of application No. 17/739,835, filed on May 9, 2022, now Pat. No. 11,793,725.

(51) Int. Cl.
| | |
|---|---|
| *A61J 7/00* | (2006.01) |
| *A61J 7/02* | (2006.01) |
| *A61J 7/04* | (2006.01) |
| *G06F 21/32* | (2013.01) |
| *G16H 20/13* | (2018.01) |

(52) U.S. Cl.
CPC .............. *A61J 7/0076* (2013.01); *A61J 7/02* (2013.01); *A61J 7/0418* (2015.05); *A61J 7/0427* (2015.05); *A61J 7/0481* (2013.01); *G06F 21/32* (2013.01); *G16H 20/13* (2018.01); *A61J 2200/30* (2013.01); *A61J 2205/10* (2013.01)

(58) Field of Classification Search
CPC ...... A61J 7/0076; A61J 7/0427; A61J 7/0418; A61J 7/02; A61J 7/0481; A61J 2200/30; A61J 2205/10; G16H 20/13; G06F 21/32
See application file for complete search history.

(56) References Cited

U.S. PATENT DOCUMENTS

| | | |
|---|---|---|
| 8,082,452 B2 | 12/2011 | Jajodia |
| 8,566,269 B2 | 10/2013 | Jajodia et al. |
| 9,203,861 B2 | 12/2015 | Albanese et al. |
| 9,436,822 B2 | 9/2016 | Ghosh et al. |
| 9,846,588 B2 | 12/2017 | Ghosh et al. |
| 10,709,643 B2 | 7/2020 | Hsu |
| 10,956,184 B2 | 3/2021 | Ghosh et al. |
| 11,100,741 B2 | 8/2021 | Rahilly et al. |
| 11,227,675 B2 | 1/2022 | Bulleit et al. |
| 11,289,182 B2 * | 3/2022 | Mousseau ............. A61J 7/0427 |
| 11,521,444 B1 * | 12/2022 | Badik ................ G07C 9/00912 |

(Continued)

*Primary Examiner* — Michael Collins
(74) *Attorney, Agent, or Firm* — Raj S. Dave; Dave Law Group LLC

(57) ABSTRACT

Embodiments relate to a system comprising a drug dispenser; a user interface to receive a user information; a bio-feedback monitoring device to monitor at least one vital of a user as an input to the bio-feedback monitoring device; a communication module; a processor; a database; a memory; wherein the processor is communicatively coupled with the memory; and wherein the processor is configured to: receive a prescription; dispense a drug through the drug dispenser on authenticating the user information with at least one vital of the user and the prescription; update an inventory of the drug through the communication module; log record of dispensing of the drug; maintain a ledger of the record of dispensing of the drug, use blockchain technology. The output of the bio-feedback monitoring device controls a quantity of drug dispensed from the drug dispenser.

20 Claims, 19 Drawing Sheets

(56) References Cited

U.S. PATENT DOCUMENTS

| | | | |
|---|---|---|---|
| 11,633,539 B1* | 4/2023 | Badik | G16H 20/17 |
| | | | 604/503 |
| 11,663,317 B2* | 5/2023 | Mousseau | H04W 12/08 |
| | | | 726/17 |
| 11,688,499 B2* | 6/2023 | Mousseau | G16H 40/67 |
| | | | 700/231 |
| 11,793,725 B1* | 10/2023 | Badik | G16H 40/67 |
| 2010/0054481 A1 | 3/2010 | Jajodia et al. | |
| 2010/0058456 A1 | 3/2010 | Jajodia et al. | |
| 2014/0245014 A1 | 8/2014 | Tuck et al. | |
| 2016/0022542 A1 | 1/2016 | Lehmann et al. | |
| 2017/0180137 A1 | 6/2017 | Spanier et al. | |
| 2018/0020008 A1 | 1/2018 | Schoof | |
| 2019/0035499 A1 | 1/2019 | Daya | |
| 2019/0080791 A1 | 3/2019 | Wolf et al. | |
| 2020/0273578 A1 | 8/2020 | Kutzko et al. | |
| 2020/0279632 A1 | 9/2020 | Mercolino et al. | |
| 2021/0027875 A1 | 1/2021 | Paydar et al. | |
| 2021/0183480 A1 | 6/2021 | Swarnam et al. | |
| 2021/0249112 A1 | 8/2021 | Mercolino et al. | |
| 2021/0343404 A1 | 11/2021 | Hunt et al. | |
| 2021/0398635 A1 | 12/2021 | Alanazi | |
| 2022/0059204 A1 | 2/2022 | Swarnam et al. | |
| 2022/0131699 A1 | 4/2022 | Kimmel et al. | |
| 2022/0367022 A1* | 11/2022 | Mousseau | G16H 20/10 |

\* cited by examiner

SMART DISPENSER

CROSS-REFERENCE TO RELATED APPLICATIONS

This application is a Continuation of U.S. patent application Ser. No. 17/739,835, filed on May 9, 2022; the contents of which are incorporated herein in their entirety by reference.

FIELD OF THE INVENTION

This invention relates to a dispensing system. The invention more particularly relates to a tamper proof smart dispensing system and method thereof.

BACKGROUND

In this section the prior art relevant to the field is cited.

"A device includes a reservoir for holding an article that has thereon and a dispenser for dispensing the articles from the reservoir. A deactivation mechanism may deactivate medicament held within the reservoir." [Source: Integrated device and system for drug dispensing; published as US20210249112A1 on Aug. 12, 2021]

"A pill dispensing system and associated methods are configured for managing the distribution of pills to a patient. In at least one embodiment, an at least one tamper-proof pill storage container provides an at least one pill magazine positioned within a housing of the pill storage container and configured for storing and selectively dispensing a plurality of pills through a pill outlet provided by the housing. A patient application, residing in memory on an at least one patient device under the control of the patient, is in selective communication with the at least one pill storage container. An at least one monitoring device is in selective communication with the patient application, the at least one monitoring device configured for assisting the patient application with monitoring an at least one vital of the patient." [Source: Tamper-proof pill dispensing system and methods of use; published as U.S. Ser. No. 10/709,643B2 on Jul. 14, 2020]

"Example implementations relate to a drug dispenser. For example, a dispenser may include a processor in communication with a server accessible to a doctor capable of prescribing a drug to a patient and a pharmacist capable of providing the drug to the patient. The processor may receive instructions relating to administration of the drug to the patient. The instructions may specify a timing and an amount of the drug to be administered and an identity of the patient. The dispenser may include a timer to provide a notification based on the timing specified in the instructions and an identifier mechanism to determine an identity of a person attempting to access the drug. The processor may provide the amount of the drug based on the instructions if the identity of the person is the identity of the patient." [Source: Drug dispenser; published as US20200246225A1 on Aug. 6, 2020]

There is a need for smart dispensers that solve the problem of the prior art. There is a need to make the drug dispensing safe for users to avoid drug overdose and to keep the drug dispenser from hackers and thereby avoiding potential misuse of the drug.

SUMMARY

An embodiment relates to a system comprising: a drug dispenser; a user interface; a biofeedback monitoring device; a communication module; a processor; and a memory. The processor is communicatively coupled with the memory; and wherein the processor is configured to receive a user information through the user interface; authenticate the user information; receive at least one vital of a user as an input to the bio-feedback monitoring device; receive a prescription; dispense a drug through the drug dispenser; update an inventory of the drug through the communication module; maintain a log of record of dispensing of the drug; maintain a ledger of the record of dispensing of the drug, using blockchain technology. An output of the biofeedback monitoring device controls a quantity of drug dispensed from the drug dispenser.

In an embodiment of the system, the system further comprises a cyber security module; and wherein the system is secured through the cyber security module.

In an embodiment of the system, the user information comprises: a unique identity of the user, and a biometric information of the user.

In an embodiment of the system, the system comprises a drug storage. The user interface further comprises an authentication sensor; a keypad; a touchpad; a scanner; and a RFID reader; and wherein the scanner comprises a Universal Product Code indicia scanner, a Quick Response code scanner, a high-capacity color barcode scanner, and an unpowered near-field communication scanner; and a prescription scanner. The processor is operable to receive the unique identity of the user through the user interface; authenticate the user by matching credentials of the unique identity against a record of patients and a record of practitioners; receive the biometric information of the user through the authentication sensor; authenticate the user by matching credentials of the biometric information against the record of practitioners and the record of patients; receive the prescription for dispensing from the user through the prescription scanner; check and authenticate dispensing of the drug with the inventory of the drug according to the user information; and dispense the drug from the drug storage through the drug dispenser.

In an embodiment of the system, the system is in communication with a server through the communication module.

In an embodiment of the system, the server comprises a database.

In an embodiment of the system, the server comprises a local server, a remote server, and a cloud server.

In an embodiment of the system, the user comprises a patient and a practitioner.

In an embodiment of the system, the bio-feedback monitoring device receives at least one vital to ensure that the user comprises the patient.

In an embodiment of the system, the authentication of the user comprises a second level of authentication.

In an embodiment of the system, the unique identity comprises a unique identification number, an RFID tag, a password, a barcode, and a Quick response QR code.

In an embodiment of the system, the biometric information comprises a fingerprint, an eyeblink, a retina scan, an iris scan, an eye scan, and a facial image scan.

In an embodiment of the system, the second level of authentication comprises the unique identity of the user and the biometric information of the user.

In an embodiment of the system, the dispensing of the drug is locked if the credentials of the unique identity do not match with the record of practitioners and the record of patients in the database.

In an embodiment of the system, the dispensing of the drug is locked if the credentials of the biometric information does not match with the record of practitioners and the record of patients in the database.

In an embodiment of the system, an authorized owner of the system is able to unlock the drug dispenser for further dispensing.

In an embodiment of the system, the unique identity of the user, and the biometric information of the user is registered in the database during registration of the user.

In an embodiment of the system, the at least one vital of the user comprises at least one of a pupil dilation of the user, a breathing rate of the user, a heart rate of the user and a blood pressure of the user.

In an embodiment of the system, the at least one vital of the user is registered in the database during registration of the user.

In an embodiment of the system, the registration of the user comprises: a name, a gender, an age, a disease, a type of treatment going on, a symptom of the disease, other ailment, an allergy related information, the biometric information, unique id information, a range of values of at least one vital of the user, physiological information, biological marker of user, drug prescription, a scheduled time to take the drug.

In an embodiment of the system, the at least one vital received by the system is monitored by comparing it with a range of values of the at least one vital of the user in the database.

In an embodiment of the system, the system comprises an alarm to generate an alert through the alarm to notify the practitioner if the at least one vital of the user monitored is abnormal; and wherein the at least one vital is abnormal if the at least one vital received by the system is not within the range of values of the at least one vital of the user in the database.

In an embodiment of the system, the drug dispenser is locked for further dispensing if the at least one vital of the user monitored is abnormal.

In an embodiment of the system, the prescription is received through the user interface.

In an embodiment of the system, the prescription is received from a digital medium and as a blockchain token.

In an embodiment of the system, the digital medium comprises a message, and an email.

In an embodiment of the system, the processor interacts with the server to check a drug name, a last dispensing time, a dosage time, a quantity of the drug delivered to the user in a day, quantity of the drug accessed by the user in the day before dispensing the drug to the user.

In an embodiment of the system, the quantity of the drug dispensed is in milligrams and milliliters.

In an embodiment of the system, the drug comprises a controlled substance, an opioid, a narcotic drug, and a psychedelic drug.

In an embodiment of the system, the log of record of the dispensing is viewable on a dashboard.

In an embodiment of the system, the log of record of the dispensing is accessible to a plurality of officials.

In an embodiment of the system, the log of record of the dispensing is accessible to an authorized third-party official for unbiased monitoring.

In an embodiment of the system, the log of record of the dispensing comprises a name of drug, a time, a date, a day, a month, a year, the quantity of the drug dispensed, name of the user receiving the drug, and a quantity of drug remaining.

In an embodiment of the system, the log of record of the dispensing is encrypted by the system.

In an embodiment of the system, the drug dispenser is tamper proof.

In an embodiment of the system, the inventory of the drug comprises a name of drug, dispensing time, a date, a day of a week, a month, a year, quantity of the drug dispensed, name of first user, a dosage time, a quantity of the drug delivered to the first user in a day, name of second user receiving the drug, quantity of the drug accessed by the second user in the day and a quantity of drug remaining.

In an embodiment of the system, the system is a Drug Enforcement Administration compliant system.

An embodiment relates to a method comprising receiving a user information through a system; authenticating the user information; receiving at least one vital of a user as an input to a bio-feedback monitoring device; receiving a prescription; dispensing a drug through a drug dispenser; updating an inventory of the drug by the system; maintaining a log of record of dispensing of the drug; maintaining a ledger of record of dispensing of the drug using blockchain technology. An output of the bio-feedback monitoring device controls a quantity of drug dispensed from the drug dispenser.

In an embodiment of the method, the system is secured through a cyber security module.

In an embodiment of the method, the user information comprises: the unique identity of the user, and the biometric information of the user.

In an embodiment of the method, the method comprises receiving the unique identity of the user by the system; authenticating the user by matching credentials of the unique identity against a record of patients and a record of practitioners; receiving the biometric information of the user by the system; authenticating the user by matching credentials of the biometric information against the record of practitioners and the record of patients; receiving the prescription for dispensing from the user through the system; checking and authenticating the dispensing of the drug with the inventory of the drug according to the user information; and dispensing the drug from a drug storage through the drug dispenser.

In an embodiment of the method, the method comprises: communicating with a server through a communication module; and wherein the server comprises a database.

In an embodiment of the method, the user comprises a patient and a practitioner.

In an embodiment of the method, the method comprises receiving the at least one of the vital as the input to the bio-feedback monitoring device when the user comprises the patient.

In an embodiment of the method, the authenticating of the user comprises a second level of authentication.

In an embodiment of the method, the receiving the unique identity comprises receiving a unique identification number, an RFID tag, a password, a barcode, and a Quick response QR code.

In an embodiment of the method, the receiving the biometric information comprises receiving a fingerprint, an eyeblink, a retina scan, an iris scan, an eye scan, and a facial image scan.

In an embodiment of the method, the second level of authentication comprises the unique identity of the user, and the biometric information of the user.

In an embodiment of the method, the method comprises locking the drug dispenser for further dispensing if the credentials of the unique identity do not match with the record of practitioners and the record of patients in the database.

In an embodiment of the method, the method comprises locking the drug dispenser for further dispensing if the credentials of the biometric information does not match with the record of practitioners and the record of patients in the database.

In an embodiment of the method, the method comprises an authorized owner of the system to be able to unlock the drug dispenser.

In an embodiment of the method, the method comprises registering the unique identity of the user, and the biometric information of the user in the database during registration of the user.

In an embodiment of the method, the method comprises receiving the at least one vital of the user comprising at least one of a pupil dilation of the user, a breathing rate of the user, a heart rate of the user and a blood pressure of the user.

In an embodiment of the method, the method comprises registering the at least one vital of the user in the database during registration of the user.

In an embodiment of the method, the registration of the user comprises receiving a name, a gender, an age, a disease, a type of treatment going on, a symptom of the disease, other ailment, an allergy related information, the biometric information, unique id information, a range of values of at least one vital of the user, physiological information, biological marker of user, drug prescription, a scheduled time to take the drug by the system.

In an embodiment of the method, receiving the at least one vital comprises monitoring by the system by comparing it with the range of values of the at least one vital of the user in the database.

In an embodiment of the method, the method comprises generating an alert through an alarm to notify a practitioner if the at least one vital of the user monitored is abnormal; and wherein the at least one vital of the user monitored is abnormal if the at least one vital received by the system is not within the range of values of the at least one vital of the user in the database.

In an embodiment of the method, method comprises locking the drug dispenser for further dispensing if the at least one vital of the user monitored is abnormal with a major difference in the range of values of at least one vital of the user.

In an embodiment of the method, the method comprises receiving the prescription from a digital medium and as a blockchain token; and wherein the digital medium comprises a message, and an email.

In an embodiment of the method, the method comprises interacting with the server to check a drug name, a last dispensing time, a dosage time, a quantity of the drug delivered to the user in a day, quantity of the drug accessed by the user in the day before dispensing the drug to the user.

In an embodiment of the method, the quantity of the drug dispensed is in milligrams and milliliters.

In an embodiment of the method, the method is for dispensing the drug comprising a controlled substance, an opioid, a narcotic drug, and a psychedelic drug.

In an embodiment of the method, the method further comprises viewing the log of record of the dispensing on a dashboard.

In an embodiment of the method, the log of record of the dispensing is accessible to a plurality of officials.

In an embodiment of the method, the log of record of the dispensing is accessible to an authorized third-party official for unbiased monitoring.

In an embodiment of the method, the log of record of the dispensing comprises name of drug, a time, a date, a day, a month, a year, quantity of the drug accessed, name of the user receiving the drug, and a quantity of drug remaining.

In an embodiment of the method, the log of record of the dispensing is encrypted by the system In an embodiment of the method, the method is for tamper proof drug dispensing.

In an embodiment of the method, the inventory of the drug comprises a name of drug, dispensing time, a date, a day of a week, a month, a year, quantity of the drug dispensed, name of first user, a dosage time, a quantity of the drug delivered to the first user in a day, name of second user receiving the drug, quantity of the drug accessed by the second user in the day and a quantity of drug remaining.

According to an embodiment, it is a system comprising, a device; a communication module communicating with a server; a user interface; a bio-feedback monitoring device; a drug dispenser; a database; and a cyber security module.

In an embodiment, the cyber security module further comprises an information security management module providing isolation between the system and the server.

In an embodiment, the information security management module is operable to, receive data from at least one of the user interface, the bio-feedback monitoring device, the drug dispenser, and the database, exchange a security key at a start of the communication between the communication module and the server, receive the security key from the server, authenticate an identity of the server by verifying the security key, analyze the security key for a potential cyber security threat, negotiate an encryption key between the communication module and the server, encrypt the data; and transmit the encrypted data to the server when no cyber security threat is detected.

In an embodiment, the information security management module is operable to exchange a security key at a start of the communication between the communication module and the server, receive the security key from the server, authenticate an identity of the server by verifying the security key, analyze the security key for a potential cyber security threat, negotiate an encryption key between the system and the server, receive encrypted data from the server, decrypt the encrypted data, perform an integrity check of the decrypted data and transmit the decrypted data to at least one of the user interface, the bio-feedback monitoring device, the drug dispenser, and the database through the communication module when no cyber security threat is detected.

In an embodiment, the information security management module is configured to raise an alarm when the cyber security threat is detected.

In an embodiment, the system of claim 4, wherein the information security management module is configured to raise an alarm when the cyber security threat is detected.

In an embodiment, the information security management module is configured to discard the encrypted data received if the integrity check of the encrypted data fails.

In an embodiment, the information security management module is configured to check the integrity of the encrypted data by checking accuracy, consistency, and any possible data loss during the communication through the communication module.

In an embodiment, the information security management module is configured to perform asynchronous authentication and validation of the communication between the communication module and the server.

In an embodiment, a perimeter network provides an extra layer of protection.

In an embodiment, the perimeter network protects the system from a cyber security threat by using a plurality of firewalls.

An embodiment relates to a system comprising a drug dispenser; a cyber security module; a communication module; a processor; and a memory. The processor is communicatively coupled with the memory. The processor is configured to: receive at least one vital of a user as an input to a bio-feedback monitoring device; receive user information of the user; receive a prescription; dispense a drug through the drug dispenser; update an inventory of the drug through the communication module; log record of dispensing of the drug; and maintain a ledger of the record of dispensing of the drug, using blockchain technology; and wherein the system is secured through the cyber security module.

An embodiment relates to a system comprising a drug dispenser; a user interface to receive a user information; a bio-feedback monitoring device to monitor at least one vital of a user as an input to the bio-feedback monitoring device; a communication module; a cyber security module; a processor; a database; and a memory. The processor is communicatively coupled with the memory. The processor is configured to receive a prescription; dispense a drug through the drug dispenser upon authenticating the user information, monitor at least one of the vital of the user; update an inventory of the drug through the communication module; log record of dispensing of the drug; maintain a ledger of the record of dispensing of the drug, using blockchain technology. An output of the bio-feedback monitoring device controls a quantity of drug dispensed from the drug dispenser. The system is secured through the cyber security module.

DETAILED DESCRIPTION

Definitions and General Techniques

Figure 1A:
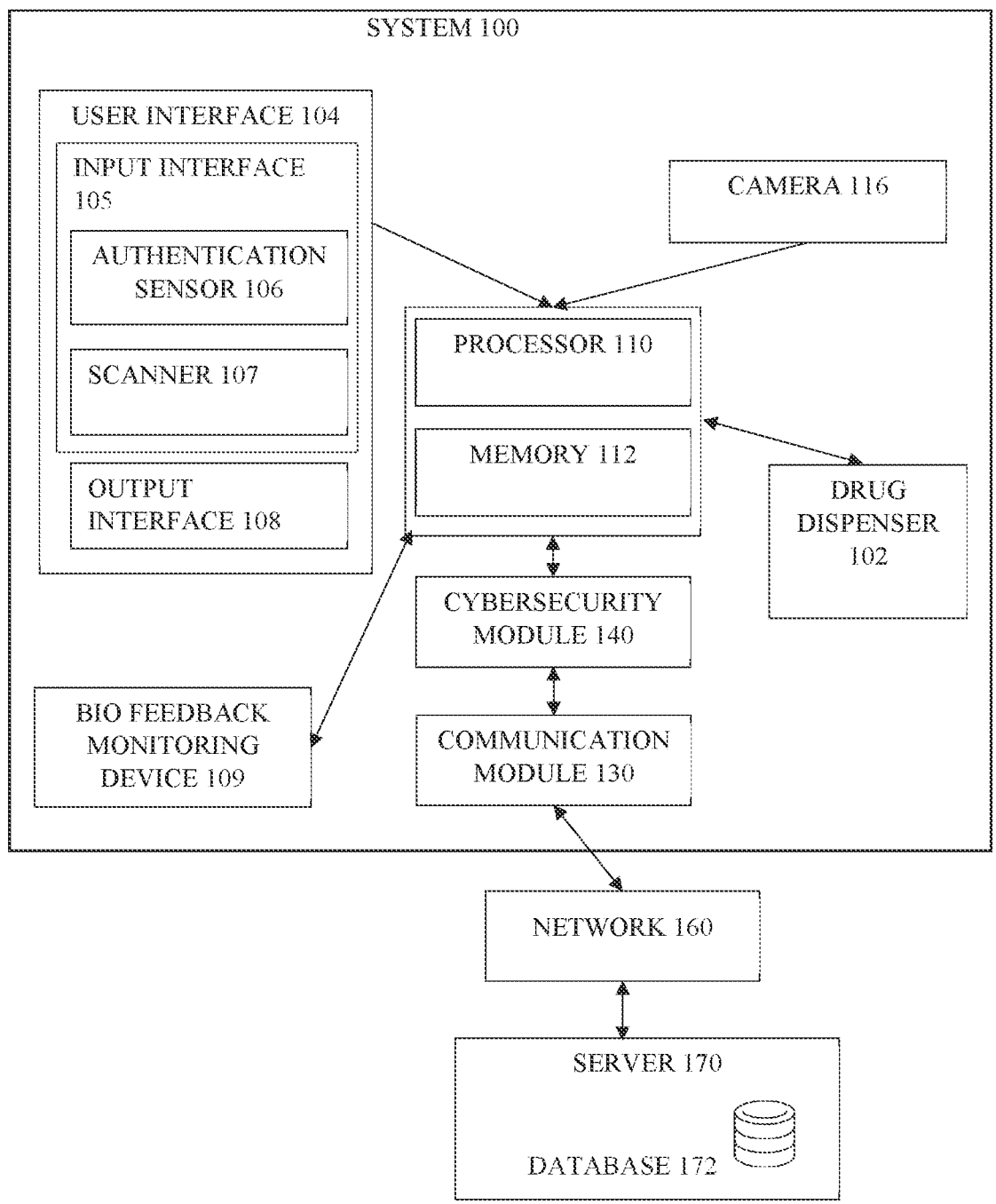
FIG. 1A shows a block level diagram of a smart dispensing system.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denotes the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The term "comprising," which is synonymous with "including," "containing," or "characterized by" here as used herein refers to being inclusive or open-ended, and does not exclude additional, unrecited elements or method steps, unless the context clearly requires otherwise.

The terms "couple", "coupled", "couples", "coupling", and the like should be broadly understood and refer to as connecting two or more elements mechanically, electrically, and/or otherwise. Two or more electrical elements may be electrically coupled together, but not be mechanically or otherwise coupled together. Coupling may be for any length of time, e.g., permanent, or semi-permanent or only for an instant. "Electrical coupling" includes electrical coupling of all types. The absence of the word "removably", "removable", and the like near the word "coupled", and the like does not mean that the coupling, etc. in question is or is not removable.

As defined herein, two or more elements or modules are "integral" or "integrated" if they operate functionally together. As defined herein, two or more elements are "non-integral" if each element can operate functionally independently.

The term "network" as used herein refers to a set of computers sharing resources located on or provided by network nodes. The computers use common communication protocols over digital interconnections to communicate with each other. These interconnections are made up of telecommunication network technologies, based on physically wired, optical, and wireless radio-frequency methods that may be arranged in a variety of network topologies. The nodes of a computer network may include personal computers, servers, networking hardware, or other specialized or general-purpose hosts. The network may include a cloud network.

The term "server" as used herein refers to A server is a computer or system that provides resources, data, services, or programs to other computers, known as clients, over a network. In theory, whenever computers share resources with client machines, they are considered servers. There may be physical servers or virtual servers. The server may be a local server or a remote server.

As used herein, a "database" is a collection of information that is organized so that it can be easily accessed, managed, and updated. Computer databases typically contain aggregations of data records or files.

Implementations may be realized in a computing system that includes a back-end component, e.g., as a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components. The components of the system may be interconnected by any appropriate form or medium of digital data communication, e.g., a communication network. Examples of communication networks include a local area network (LAN) and a wide area network (WAN), e.g., the Intranet and Internet.

The computing system may include clients and servers. A client and server are generally remote from each other and typically interact through a communication network. The relationship of client and server arises by virtue of computer programs running on the respective computers and having a client-server relationship to each other.

Embodiments of the present invention may comprise or utilize a special purpose or general purpose computer including computer hardware. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly distinct kinds of computer-readable media: physical computer-readable storage media and transmission computer-readable media.

Computer-executable instructions comprise, for example, instructions and data which cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described. Rather, the described features and acts are disclosed as example forms of implementing the claims.

Processors suitable for the execution of a computer program include, by way of example, both general and special purpose microprocessors, and any one or more processors of any appropriate kind of digital computer. Generally, a processor will receive instructions and data from a read-only memory or a random-access memory or both. Elements of a computer can include a processor for performing instructions and one or more memory devices for storing instructions and data. Generally, a computer will also include, or be operatively coupled to receive data, transfer data or both, to/from one or more mass storage devices for storing data e.g., magnetic disks, magneto optical disks, optical disks, or solid-state disks. However, a computer need not have such mass storage devices. Moreover, a computer may be embedded in another device, e.g., a mobile telephone, a personal digital assistant (PDA), a mobile audio player, a Global Positioning System (GPS) receiver, etc. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD ROM) disks, Digital Versatile Disk-Read-Only Memory (DVD-ROM) disks) and solid-state disks. The processor and the memory may be supplemented by, or incorporated in, special purpose logic circuitry.

To provide for interaction with a user, implementations may be realized on a computer having a display device (e.g., a cathode ray tube (CRT) or liquid crystal display (LCD) monitor) for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Unless otherwise defined herein, scientific, and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, medical smart storage are described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

Example embodiments, as described below, may be used to provide a system a. It will be appreciated that the various embodiments discussed herein need not necessarily belong to the same group of embodiments and may be grouped into various other embodiments not explicitly disclosed herein. In the following description, for purposes of explanation, numerous specific details are set forth in order to provide a thorough understanding of the various embodiments.

Implementations and all of the functional operations described in this specification may be realized in digital electronic circuitry, or in computer software, firmware, or hardware.

A software program (also known as a program, software, executable code, or instructions) may be written in any appropriate form of programming language, including compiled or interpreted languages, and it may be deployed in any appropriate form, including as a standalone program or as a module, component, subroutine, or other unit suitable for use in a computing environment.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may generally be integrated together in a single software product or packaged into multiple software products.

Even though particular combinations of features are recited in the claims and/or disclosed in the specification, these combinations are not intended to limit the disclosure of possible implementations. Other implementations are within the scope of the following claims. For example, the actions recited in the claims may be performed in a different order and still achieve desirable results. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

Further, the methods may be practiced by a computer system including one or more processors and computer-readable media such as computer memory. In particular, the computer memory may store computer-executable instructions that when executed by one or more processors cause various functions to be performed such as the acts recited in the embodiments.

The following terms and phrases, unless otherwise indicated, shall be understood to have the following meanings.

The term "drug dispenser" as used herein refers to a device which releases medication at specified times.

The term "drug storage" as referred to herein, is a vault or a storage box compliant to the Drug Enforcement Administration (DEA) under 12 CFR 1302.72 which pharmaceutical products and materials are kept ensuring their stable forms are retained up to the point of use or till it reaches the consumer. The loss of potency during storage may influence the efficacy and safety of pharmaceuticals.

The term "drug" as referred to herein is a chemical which is used as a medicine.

The term "drug container" as used herein refers to a container for a pharmacopeial article that is intended to contain a drug substance.

The term "communication module" is a module that facilitates communication, that is, it enables transmission and receiving of data from the input and output interfaces to the processor. It also enables communication between the peripheral devices connected with the processor like display, camera, remote servers, and databases. A communication module may be a wired connection between the components or a wireless communication module.

The term "log record" as used herein is collecting and storing data over a period of time in order to analyze specific trends or record the data-based events/actions of a system, network, or information technology (IT) environment. It enables the tracking of all interactions through which data, files, or applications are stored, accessed, or modified on a storage device or application.

The term "access of the drug" as used herein refers to the ability to take the drug out from the drug storage by an authenticated user.

The term "biofeedback monitoring" as used herein refers to the devices and programs connected to electrical sensors that help in receiving information about physiological and mental state of a wearer's body. The physiological state of the wearer's body comprises a breathing rate of a person, a heart rate of a person, a pupil dilation of the person and blood pressure of the person.

The term "vital" as used herein refers to measurements of the body's most basic functions. The four main vital signs routinely monitored by medical professionals and health care providers include the following: body temperature, pulse rate, respiration rate (rate of breathing), blood pressure. In the current application pupil dilation is also measured.

The term "actuating mechanism" as used herein refers to a mechanism or a device that produces a motion by converting energy and signals going into the system. The actuating mechanism herein used is to open the outlet of the drug dispenser.

The term "outlet" as used herein refers to an opening that allows an item to be dropped out.

The term "ledger" as used herein refers to a collection of the transactions recorded. Here transactions mean the quantity of drugs in and out of the drug storage, the number of drugs accessed, the time of access, the quantity of drugs refilled in the storage and the balance quantity of the drug remaining in the drug storage.

The term "authentication sensor" as used herein refers to a sensor to perform user authentication and receives the identity of a user attempting to gain access to a network or computing resource by authorizing a human-to-machine transfer of credentials during interactions on a network to confirm a user's authenticity. Authentication sensor keeps unauthorized users from accessing sensitive information.

The term "sensor" as used herein refers to a device that detects or measures a physical property and enables the recording, presentation or response to such detection or measurement using processor and optionally memory. A sensor and processor can take one form of information and convert such information into another form, typically having more usefulness than the original form. For example, a sensor may collect raw physiological or environmental data from various sensors and process this data into a meaningful assessment, such as pulse rate, blood pressure, or air quality using a processor. A "sensor" herein can also collect or harvest acoustical data for biometric analysis (by a processor) or for digital or analog voice communications. A "sensor" can include any one or more of a physiological sensors (e.g., blood pressure, heartbeat, etc.), a biometric sensor (e.g., a heart signature, a fingerprint, etc.), an environmental sensor (e.g., temperature, particles, chemistry, etc.), a neurological sensor (e.g., brainwaves, electroencephalogram (EEG) etc.), or an acoustic sensor (e.g., sound pressure level, voice recognition, sound recognition, etc.), among others. A variety of microprocessors or other processors may be used herein. Although a single processor or sensor may be represented in the figures, it should be understood that the various processing and sensing functions can be performed by a number of processors and sensors operating cooperatively, or by a single processor and sensor arrangement that includes transceivers and numerous other functions.

As used herein, the term "component" is intended to be broadly construed as hardware, firmware, and/or a combination of hardware and software.

As used herein, the term "API" stands for Application Programming Interface. It is an interface that defines interactions between multiple software applications or mixed hardware-software intermediaries. It defines the kinds of calls or requests that can be made, how to make them, the data formats that should be used, the conventions to follow, etc. It can also provide extension mechanisms so that users can extend existing functionality in several ways and to varying degrees. An API can be entirely custom, specific to a component, or designed based on an industry-standard to ensure interoperability. Through information hiding, APIs enable modularity, allowing users to use the interface independently of the implementation. Web APIs is now the most common meaning of the term API. There are also APIs for programming languages, software libraries, computer operating systems, and computer hardware.

The term "communicatively coupled" as used herein refers to devices connected in a way that permits communication.

The term "controller" as used herein refers to the component of a system that functions as the system controller. A controller typically sends program messages to and receives response messages from devices. A functional unit in a computer system that controls one or more units of the peripheral equipment. Synonym: peripheral control unit. See also: input-output controller; dual channel controller. In robotics, a controller takes as input desired and measured position, velocity or other pertinent variables and whose output is a drive signal to a controlling motor or activator. A device through which one can introduce commands to a control system.

The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to a suitable receiver apparatus.

The term "second level of authentication" used herein refers to the process or action of verifying the identity of a user or process, wherein the identity of the user is verified by corresponding data, in the present application a user may be a patient and practitioner.

The term "unique identity" as used herein refers to a means of one or more features enabling that person to be distinguished from another data subject.

The term "biometric information" as used herein refers to any means by which a person can be uniquely identified by evaluating one or more distinguishing biological traits. These biological identifiers include fingerprints, hand and earlobe geometries, retina patterns, voice prints and written signatures.

The term "patient" as used herein refers to a person receiving or registered to receive medical treatment.

The term "practitioner" as used herein refers to a person who is skilled in the science of medicine. For example, a general practitioner for minor illnesses, a doctor, and a surgeon.

The term "record of practitioners" as used herein refers to a record of the data related to the practitioners in a hospital or clinic, or the practitioner. The record of practitioner comprises name of practitioner, age of practitioner, gender of the patient, qualification of the practitioner, experience in years, biometric information, unique id information, name of patient to be under the practitioner's supervision.

The term "record of patient" as used herein refers to a record of the data related to the patient undergoing treatment. The record of patient comprises a name of patient, age of the patient, gender of the patient, a disease, a type of treatment going on, symptoms of the disease, other diseases, allergies, biometric information, unique id information, physiological information, biological marker of patient, drug prescription, scheduled timings to take the drug.

The term "scheduled time" as used herein refers to appointment, assignment, or designation for a fixed time.

The term "physical conditioning parameters" as used herein refers to the environmental condition which affects the contents in the drug storage. The physical conditioning parameters here refer to temperature, humidity, and pressure inside the drug storage.

The term "RFID tag" and "RFID reader" as used herein refers to Radio-frequency identification (RFID) tags and readers that use electromagnetic fields to automatically identify and track tags attached to objects. An RFID system consists of a tiny radio transponder, a radio receiver and transmitter. When triggered by an electromagnetic interrogation pulse from a nearby RFID reader device, the tag transmits digital data, usually an identifying inventory number, back to the reader. This number can be used to track inventory goods. Passive tags are powered by energy from the RFID reader's interrogating radio waves.

The term "prescription detail" used herein refers to a name of the drug, an amount of drug taken at any one time and the time to take the drug. A dose is a measured quantity of a medicine, nutrient, or pathogen which is delivered as a unit. The greater the quantity delivered, the larger the dose. Doses are most commonly measured for compounds in medicine. The term is usually applied to the quantity of a drug or other agent administered for therapeutic purposes but may be used to describe any case where a substance is introduced to the body.

The term "controlled substance" as used herein refers to A controlled substance is generally a drug or chemical whose manufacture, possession and use is regulated by a government, such as illicitly used drugs or prescription medications that are designated by law.

The term "opioid" as used herein refers to a compound resembling opium properties or effects.

The term "narcotic" as used herein refers to a drug or other substance that affects mood or behavior and is consumed for non-medical purposes.

The term "psychedelic drug" as used herein refers to a psychotomimetic drug or hallucinogen, any of the so-called mind-expanding drugs that are able to induce states of altered perception and thought, frequently with heightened awareness of sensory input but with diminished control over what is being experienced.

As used herein, the term "dashboard" is a type of interface that visualizes particular Key Performance Indicators (KPIs) for a specific goal or process. It is based on data visualization and infographics.

The term "official" as used herein refers to a person holding public office or having official duties, especially as a representative of an organization or government department. The definition of official is authorized or is someone who holds a position of authority.

The term "third party official" as used herein refers to a person or group besides the two primarily involved in a situation. Here the person who is not directly involved with the clinic or hospital that uses the system for smart medical storage.

The term "authorized owner" as used herein refers to a person approved or assigned by the employer to perform a specific type of duty or duties or to be at a specific location or locations at the jobsite.

The term "unbiased monitoring" used herein refers to observing, checking, or maintaining regular surveillance over something over a period of time; keep under systematic review. It may be referred to as keeping an eye or keeping track of something.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers—say, 'A' is '01', 'B' is '02', and so on. For example, a message like "HELLO" will be encrypted as "0805121215," and this value will be transmitted over the network to the recipient(s).

The term "decrypt" used herein refers to the process of converting an encrypted message back to its original format. It is generally a reverse process of encryption. It decodes the encrypted information so that an authorized user can only decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damage data, steal data, or disrupt digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attack, data breaches, Denial of Service (DoS) attacks, and other attack vectors.

The term "hash value" used herein can be thought of as fingerprints for files. The contents of a file are processed through a cryptographic algorithm, and a unique numerical value—the hash value—is produced that identifies the contents of the file. If the contents are modified in any way, the value of the hash will also change significantly. Example algorithms used to produce hash values: the Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application. Data integrity refers to the accuracy and consistency (validity) of data over its lifecycle. Compromised data is of little use to enterprises, not to mention the dangers presented by sensitive data loss.

The term "alarm" as used herein refers to a trigger when a component in a system or system fails or does not perform as expected. System may enter an alarm state when a certain event occurs. An alarm Indication signal is a visual signal to indicate the alarm state. For example, the heart rate is very low, a light emitting diode (LED) may glow red alerting that it is beyond the specified limits, and it turns green when the heart rate is within specified limits. Another example could be, when a cyber security threat is detected, a network administrator may be alerted via sound alarm, a message, a glowing LED, a pop-up window, etc. Alarm indication signal may be reported downstream from a detecting device, to prevent adverse situations or cascading effects.

The term "in communication with" as used herein, refers to any coupling, connection, or interaction using electrical signals to exchange information or data, using any system, hardware, software, protocol, or format, regardless of whether the exchange occurs wirelessly or over a wired connection.

As used herein, the term "cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program. Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation. Hashing algorithms may be used to verify the integrity of data. Secure Socket Layer (SSL) and Transport Layer Security (TLS), the successor to SSL, are cryptographic protocols that may be used by networking switches to secure data communications over a network.

As used herein, the term "perimeter network" refers to a network closest to a router that is not under the enterprise or organization control. Usually, a perimeter network is the final step a packet takes traversing one of your networks on its way to the internet; and conversely the first network encountered by incoming traffic from the Internet. A network perimeter is a secured boundary between the private and locally managed side of a network, often a company's intranet, and the public facing side of a network, often the Internet. The boundary is defined as a perimeter network.

As used herein, the term "network" may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof. Furthermore, although not shown, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers. Cloud servers are located in data centers all over the world. By using cloud computing, users and companies don't have to manage physical servers themselves or run software applications on their own machines.

As used herein, the term "system hardening" is a collection of tools, techniques, and best practices to reduce vulnerability in technology applications, systems, infrastructure, firmware, and other areas. The goal of system hardening may be to reduce security risk by eliminating potential attack vectors and condensing the system's attack surface.

As used herein, the term "SHA256" stands for Secure Hash Algorithm 256-bit is a hash function and it is used for cryptographic security. Cryptographic hash algorithms produce irreversible and unique hashes. The larger the number of possible hashes, the smaller the chance that two values will create the same hash.

The term "in communication with" as used herein, refers to any coupling, connection, or interaction using electrical signals to exchange information or data, using any system, hardware, software, protocol, or format, regardless of whether the exchange occurs wirelessly or over a wired connection.

The term "module" as used herein refers to a set of standardized or independent units/parts that can be used to construct a more complex structure. A module is a combination of both hardware units and software programs to control hardware units. It refers to any known or later developed hardware, software, firmware, artificial intelligence, fuzzy logic, or combination of hardware and software that is capable of performing the functionality associated with that element.

The term "quantity of drug" as used herein refers to dosage of the drug administered to a subject at a given time or over a cumulative period of time.

An embodiment relates to a system comprising a drug dispenser; a user interface; a bio-feedback monitoring device; a communication module; a cyber security module; a processor; a memory. The processor is communicatively coupled with the memory; and the processor is configured to receive a user information through the user interface; authenticate the user information; receive at least one vital of a user as an input to the bio-feedback monitoring device; receive a prescription; dispense a drug through the drug dispenser; update an inventory of the drug through the communication module; maintain a log of record of dispensing of the drug; maintain a ledger of the record of dispensing of the drug, using blockchain technology. The output of the bio-feedback monitoring device controls a quantity of drug dispensed from the drug dispenser. The system is secured through the cyber security module.

In an embodiment, the user information comprises: a unique identity of the user, and biometric information of the user. The system further comprises a drug storage. The user interface further comprises; an authentication sensor; a keypad; a touchpad; a scanner; and a RFID reader; and wherein the scanner comprises a Universal Product Code indicia scanner, a Quick Response code scanner, a high-capacity color barcode scanner, and an unpowered near-field communication scanner a prescription scanner; and the processor is operable to: receive the unique identity of the user through the user interface; authenticate the user by matching credentials of the unique identity against a record of patients and a record of practitioners; receive the biometric information of the user through the authentication sensor; authenticate the user by matching credentials of the biometric information against the record of practitioners and the record of patients; receive the prescription for dispensing from the user through the prescription scanner; check and authenticate dispensing of the drug with the inventory of the drug according to the user information; dispense the drug from the drug storage through the drug dispenser.

In an embodiment, the system is in communication with a server through the communication module. The server comprises a database. The server comprises a local server, a remote server, and a cloud server.

In an embodiment, the user comprises a patient and a practitioner.

FIG. 1A shows a block level diagram of a system 100 for a smart dispensing system. The smart dispensing system described herein is for safe dispensing of drugs. Safe dispensing of drugs herein refers to tamper proof dispensing by tracking the vitals of a patient as well as authenticating the identity of a user. The system comprises: a drug dispenser 102; a user interface 104; a bio-feedback monitoring device 109; a communication module 130; a cyber security module 140; a processor 110; and a memory 112. The processor 110 is communicatively coupled with the memory 112, a communication module 130; and a cyber security module 140. The user interface 104 further comprises an input interface comprising an authentication sensor 105, scanner 106, a keypad; a touchpad; and a RFID reader. The scanner comprises a Universal Product Code indicia scanner, a Quick Response code scanner, a high-capacity color barcode scanner, and an unpowered near-field communication scanner. The user interface 104 also comprises an output interface 108. The output interface 108 may comprise a display device, a touch display, a buzzer, speaker, and an alarm. The system is in communication with the server 170 through the communication module 130 and a network 160. The server 170 comprises at least one of a local server, a remote server, and a cloud server. The communication module 130 connects to the server 170 through the network 160. The server comprises a database 172.

The communication module 130 can include multiple communication protocols, such as Bluetooth, 802.11a/b/g/n, and CDMA, GSM and 3G/4G/4G LTE mobile phone communication protocols. 802.11a/b/g/n and mobile phone communication protocols can be utilized by the processor 110 to contact the server for retrieving medication information relating to drug interactions, administering information, etc. In one embodiment, a cable, such as a network cable with a RJ45 connector, can be used to communicate to devices external from the drug dispenser 102. The communication module 130 and/or the cable can allow the system 100 to contact a treating health organization through the communication module 130 to relay medication compliance information and other related information for the patient's health records. The processor 110 may be configured to provide encryption and decryption when sending or receiving personal health-related information in order to maintain patient privacy; in one embodiment the data will be HIPAA (Health Insurance Portability and Accountability Act) compatible. In one embodiment, the processor 110 allows sharing of data regarding compliance, errors, and device malfunction. In addition, the processor 110 performs updates and changes to the current therapy through the server.

Figure 1B:
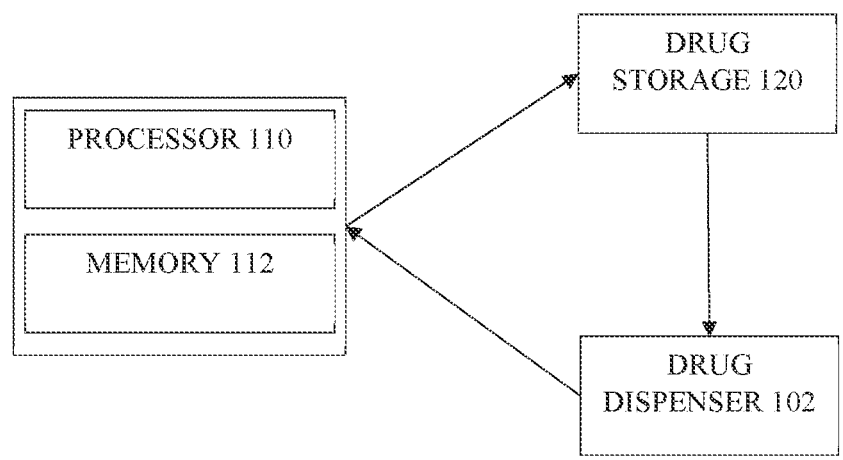
FIG. 1B shows an embodiment of the smart dispensing system connected to a drug storage.
Figure 1C:
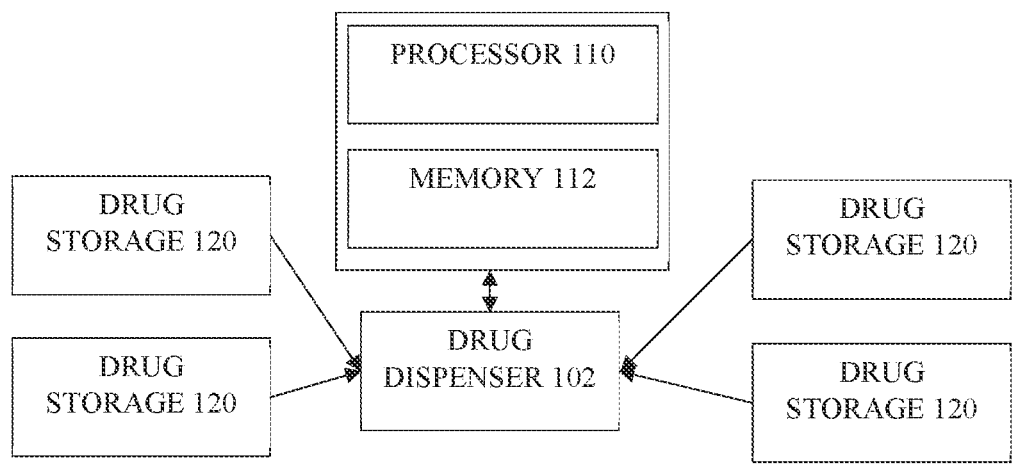
FIG. 1C shows another embodiment of the smart dispensing system connected to a drug storage.

In an embodiment, referring to FIG. 1B, the drug dispenser 102 is connected to a drug storage 120 to receive the medication cartridges, vials, or pills. The medication cartridges, vials or pills are of different quantities in different drug storages and are conveyed to the drug dispenser by conveyor belts, gravity slides and alike. The processor 110 receives the request to dispense the drug. The processor 110 transmits a signal to the drug storage to convey the drug container to the drug dispenser according to the request received In an embodiment, referring to FIG. 1C, the drug dispenser 102 is connected to a plurality of drug storages 120 to receive the medication cartridges, vials, or pills. The medication cartridges, vials or pills are of different quantities in different drug storages and are conveyed to the drug dispenser by conveyor belts, gravity slides and alike. Different kinds of drugs, pills, vials, and syringes may be stored in the drug storages 120.

Figure 2A:
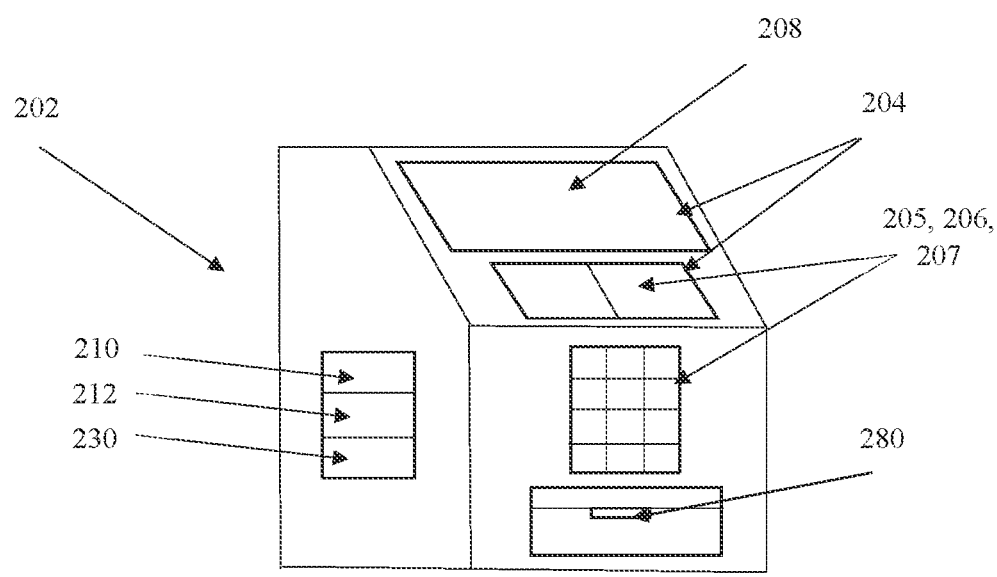
FIG. 2A shows a schematic view of the drug dispenser in an embodiment.

In an embodiment, as shown in FIG. 2A, it shows an illustration of a drug dispenser for use in a system to secure, control, and enhance medication adherence. According to one embodiment of the present invention, the drug dispenser 202 may be filled with drug containers comprising vials, syringes, pillboxes, and the like, to be delivered to a specific patient. The FIG. 2A shows the components of the drug dispenser. In that regard, it should be noted that the particular size, shape, and dimensions of drug dispenser 202 shown in the drawings is merely exemplary and is being shown for illustrative purposes. Generally speaking, the drug dispenser 202 can comprise a wireless device such as any of the devices described above with reference to FIG. 1A. The drug dispenser 202 can comprise a processor 210, memory 212, an outlet 280 and a communication module 230 and may execute software to perform the functions described here. As illustrated here, the drug dispenser 202 may also include a drug storage comprising a number of removable vessels or medication cartridges. As will be seen, these vessels or medication cartridges may be pre-loaded by a pharmacy with prescription medication for the user of the drug dispenser 202.

In an embodiment, as shown in FIG. 2A, the drug dispenser 202 comprises the user interface 204, input interface 205, the output interface 208, processor 210, memory 212, and the communication module 230 embedded on to the drug dispenser 202. The drug dispenser 202 comprises the authentication sensor 206 that is in direct communication through the communication module 230 with the processor 210 and memory 212 to allow the dispensing of the drug from the drug dispenser 202. The drug dispenser dispenses the drug, when authentication is verified, by turning on the actuating mechanism to open the outlet to dispense. If the user interface by the processor concludes a failure to authenticate, the drug dispenser prevents unauthorized dispensing of the drug containers and items stored therein. During operation, the drug dispenser may be activated, otherwise released, upon authentication of a user. The input interface 205, the output interface 207, the processor 210 and the memory 212, are mounted on the drug dispenser 202. The input interface 205 comprises an authentication sensor; a keypad; a touchpad; a scanner; and a RFID reader. The scanner comprises a Universal Product Code indicia scanner, a Quick Response code scanner, a high-capacity color barcode scanner, and an unpowered near-field communication scanner. The output interface comprises a LED display, an LCD display, a buzzer, an alarm, and a speaker.

In an embodiment, the drug dispenser 202 is connected to a plurality of drug storages to receive the medication cartridges, vials, or pills. The medication cartridges, vials or pills are of different quantities in different drug storages and are conveyed to the drug dispenser by conveyor belts, gravity slides and alike.

According to one embodiment, the drug dispenser 202 can also support multi-drug capabilities for support of dynamic, complex, and multi-provider medication regimens. The use of unit dose packaging in the cartridges accommodates complex drug regimens. Such packaging equipment permits several different drugs to be placed in a single packet, and the automated pharmacy equipment permits the packaging of sequential packets with different regimens in a given cartridge should it be necessary to include additional drugs in two or more packets. In this case the drug dispenser 202 can dispense the additional packets in sequence. Also, a multi-cartridge design of the drug dispenser 202 can permit prescription modifications from the same, or other, providers without having to change the initial cartridge. For example, if a second, short-term prescription for an antibiotic is ordered by a practitioner it can be added to the patient's drug regimen by dispensing it from a second (third or fourth) cartridge. Long term changes can be handled in the same way, except that once the primary cartridge's contents are exhausted it can be refilled with the new drug added to the single packet regimen. Also, multiple cartridges permit prescription refills prior to the primary cartridge becoming empty. The refill cartridge can be placed in the drug dispenser 202 but not used until the primary is empty. The refill can then become the primary and the empty can be returned to the pharmacy for refills. This dispensing management can be handled automatically by the drug dispenser 202 by matching the contents of the individual cartridge(s) with the patient's prescription and dispensing what is appropriate, avoiding duplicate dispensing, reordering cartridges as they approach empty, and dispensing from multiple cartridges when appropriate to fill the ordered prescription(s).

According to one embodiment, the drug dispenser 202 can additionally or alternatively manage prescription and Over the Counter (OTC) drug compatibility. The addition of this capability can be facilitated by the multiple cartridge design of the drug dispenser 202 if implemented as such. That is, multiple cartridges can be loaded with prescription and Over the Counter (OTC) drugs but dispensed only in an order, combination, or on a schedule that does not create compatibility or interaction problems. Information for identifying and managing these compatibility or interaction problems can also be encoded into the on-board memory of the individual cartridges by the pharmacy or caregiver before being dispensed.

According to one embodiment, the drug dispenser 202 can additionally or alternatively provide medication reminders to promote medication adherence. In such cases, automated audio-visual medication reminders can be delivered by the display on the top of the drug dispenser 202 and/or a mobile device that has a software application installed that enables the mobile device to communicate with the drug dispenser wirelessly, e.g., via Bluetooth, Wi-Fi, etc. The medication reminders can be programmed through the pharmacy and delivered on the memory chip embedded in the cartridge. In some cases, these reminders can also be remotely updated by the pharmacy wirelessly, e.g., via a cellular, Wi-Fi connection to the Internet, or other connection, in the event of prescription changes. In some cases, the audio-visual capabilities of the drug dispenser 202 can be used to deliver educational materials and provide a venue for virtual doctor's visits through the use of text messaging, voice messaging or live conferences.

According to one embodiment, the drug dispenser 202 can additionally or alternatively provide medication adherence monitoring and keep the professional provider/caregiver in the communication "loop". As described above, the system is capable of communicating wirelessly with the pharmacy via a cellular transceiver of the drug dispenser and/or via a Wi-Fi or other connection from the drug dispenser 202 to the Internet or other communications network. In the event that the drug dispenser 202 detects the drugs have not been taken as scheduled, the drug dispenser 202 can notify either the pharmacist, provider and/or caregiver. This can be accomplished by an application loaded on the healthcare provider's or the pharmacist's smartphone, via a text message or email, or through other messages. Another feature that can be incorporated in the drug dispenser 202 to encourage adherence are game-like software features that track and score patient's adherence performance over time and offer feedback and other benefits and awards for top performers.

According to one embodiment, the drug dispenser 202 can additionally or alternatively support delivery validation functions to provide point-to-point safe and secure medication delivery, refills and returns. In such implementations, the drug dispenser 202 can notify the pharmacy and/or provider or caregiver when a new cartridge is delivered, when it has been loaded in the drug dispenser 202, when the user dispenses medication and when the contents of a cartridge is about to be exhausted, and thereby providing an automated refill request. The refill of the cartridge can be safely and effectively accomplished using the secure cartridges as described herein. These allow the drug provider to ship a self-addressed envelope with the cartridge. When empty, or at the end of use (and unused drugs are still contained in the cartridge), the patient can place the cartridge into the envelope and drop it in a mailbox. The pharmacy can then refill the cartridge (or the unused drugs are safely disposed of), and the data stored in the memory of the cartridge can be updated at the pharmacy and the cartridge can be returned to the patient by the same method.

According to one embodiment, the drug dispenser 202 can additionally or alternatively provide automated loading and dispensing that allow pharmacy-level expertise to properly provision the system. In such implementations, rather than requiring the user, friends and/or family members, to laboriously load drug dispensing chambers with a complex prescription regimen, the drug dispenser 202 uses the pre-loaded cartridges that have been filled by professional pharmacy personnel using automated packaging systems. This not only prevents mistakes in the drug provisioning process but also prevents drug diversion and abuse that is a natural byproduct of an open, unsecured container and manual drug handling and loading in the home.

According to one embodiment, the drug dispenser 202 can additionally or alternatively provide Adverse Drug Reaction (ADR) adjudication functions which can comprise an interlock that proactively prevents ADR events and notifies providers should the system (e.g., using a third party ADR database) detect a potential ADR event. For example, the drug dispenser 202 can prevent the dispensing of the offending product(s) and notify the pharmacist or provider through wireless communication. In the meantime, the drug dispenser 202 can continue to dispense the standard regimen as it awaits updating. In some cases, an authorized pharmacist or provider may override the ADR interlock remotely after the potential ADR case has been reviewed and approved. Facilitating professional overriding of these alerts can be provided in cases where clinical situations mandate use of drugs with interaction risks (e.g., spironolactone and ACE inhibitors in heart failure).

The drug dispenser 202 may also include a user interface 204 operating dispensing and/or loading functions of the drug dispenser 202. In some cases, the user interface 204 may comprise of, or include, an authentication sensor, such as a fingerprint scanner, a fingerprint, an eyeblink scanner, a retina scanner, an iris scanner, an eye scanner, and a facial image scanner to read biometric information of a user of the drug dispenser to be used to authenticate the user before dispensing or loading of medication from or into the drug dispenser 202. For example, at a scheduled time, an alarm may sound through a speaker (not shown here) of the drug dispenser 202. In response, the user can touch the button which may also take a biometric sample to be verified and, assuming the user is authenticated, a medication packet containing the prescribed medication to be taken and this scheduled time can be dispensed from one of the medication cartridges of the drug dispenser.

The drug dispenser can also include a display such as an LCD for displaying information related to the medication and/or functions of the drug dispenser 202. For example, the display may show a schedule for dispensing medication, types of medications in the cartridges currently loaded in the drug dispenser 202, an amount of medication remaining in the medication cartridges etc. In some cases, the display may comprise a touch screen providing access to other functions and features of the drug dispenser including, but not limited to, setting and silencing alarms, initiating and/or canceling dispensing and/or loading operations, requesting refills, etc.

In an embodiment, the authentication of the user comprises a second level of authentication. The unique identity comprises a unique identification number, an RFID tag, a password, a barcode, and a Quick response (QR) code. The biometric information comprises a fingerprint, an eyeblink, a retina scan, an iris scan, an eye scan, and a facial image scan. A second level of authentication comprises the unique identity of the user and the biometric information of the user. The dispensing of the drug is locked if the credentials of the unique identity do not match with the record of practitioners and the record of patients in the database. The dispensing of the drug is locked if the credentials of the biometric information does not match with the record of practitioners and the record of patients in the database. An authorized owner of the system is able to unlock the drug dispenser for further dispensing.

In an embodiment, the unique identity of the user, and the biometric information of the user is registered in the database during registration of the user. The registration of the user comprises: a name, a gender, an age, a disease, a type of treatment going on, a symptom of the disease, other ailment, an allergy related information, the biometric information, unique id information, a range of values of at least one vital of the user, physiological information, biological marker of user, drug prescription, a scheduled time to take the drug.

In an embodiment, the at least one vital of the user comprises at least one of a pupil dilation of the user, a breathing rate of the user, a heart rate of the user and a blood pressure of the user. The at least one vital of the user is registered in the database during registration of the user. The at least one vital received by the system is monitored by comparing it with a range of values of the at least one vital of the user in the database. The system comprises an alarm to generate an alert through the alarm to notify the practitioner if the at least one vital of the user monitored is abnormal; and wherein the at least one vital is abnormal if the at least one vital received by the system is not within the range of values of the at least one vital of the user in the database. The drug dispenser is locked for further dispensing if the at least one vital of the user monitored is abnormal.

Figure 2B:
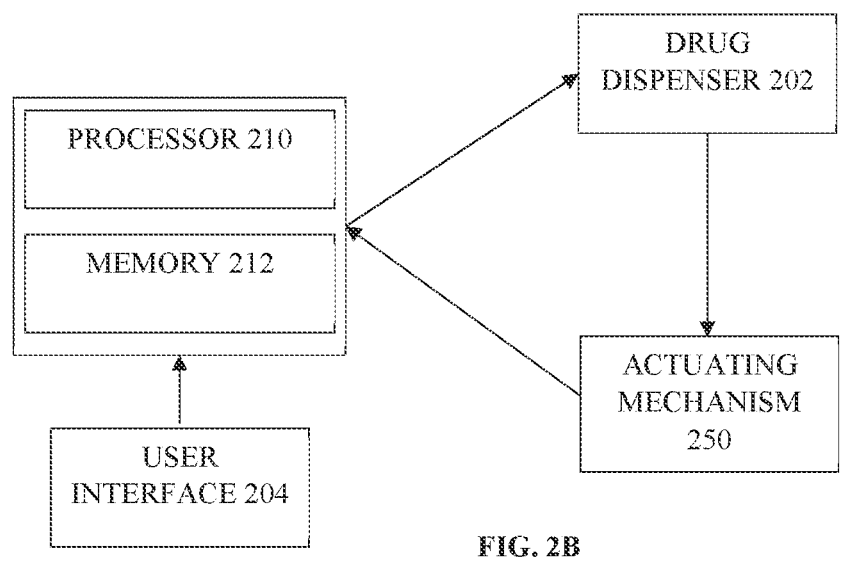
FIG. 2B shows a block diagram of the drug dispenser with the actuating mechanism.

In an embodiment as shown in FIG. 2B the drug dispenser comprises one or more actuating mechanisms 250. The processor 210 may be configured to control actuating mechanism 250 based on inputs received from the user from the user interface 204, or another device. For example, the patient may authenticate their identity and enter a prescription through the user interface 204 on the drug dispenser 202 to dispense a medication, the processor 210 in turn controls the actuating mechanism 250 to dispense the appropriate medication from one or more vials or medication cartridges from the one or more pill magazines (e.g., collection of vials). The processor 210 may be also configured to control the actuating mechanism 250 at a predetermined schedule to automatically dispense the medication at appropriate times, or in response to an external trigger received as input data.

In an embodiment, the drug dispenser 202 may be an Internet of Things device, or a "thing" embedded with electronics, software, sensors, and connectivity to enable objects to exchange data with different devices, authorities and components (authorities for e.g., doctor, pharmacy, health care providers).

Figure 2C:
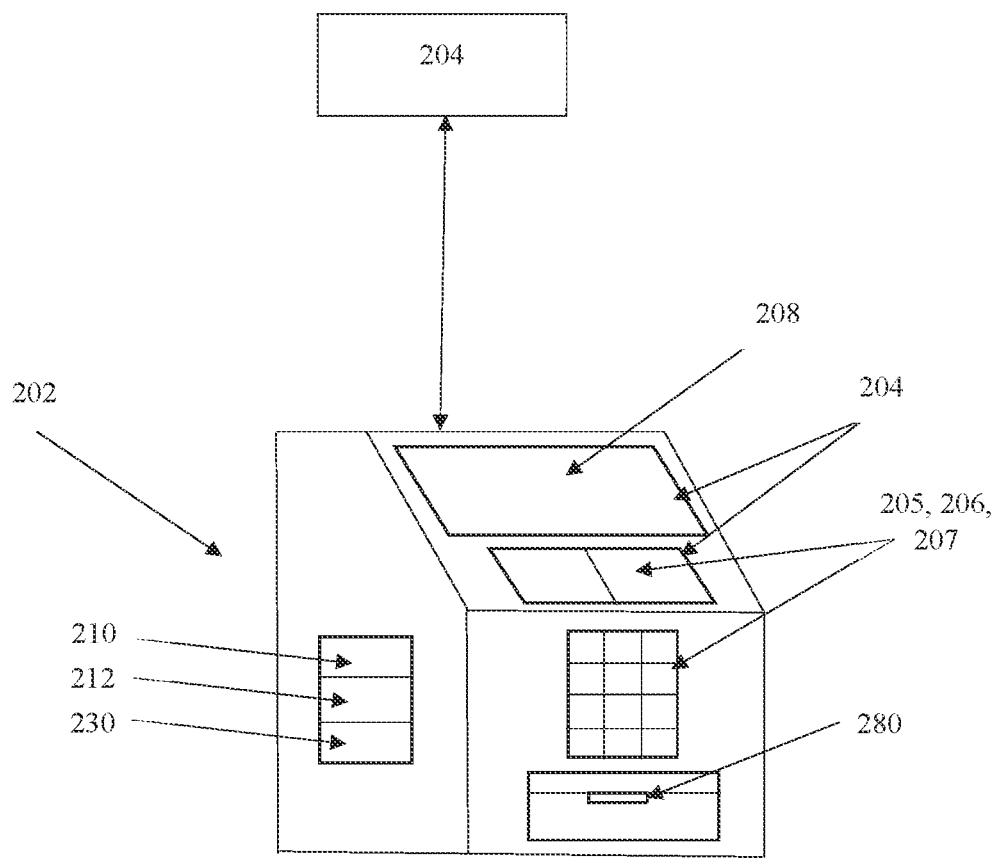
FIG. 2C shows a schematic view of the drug dispenser in another embodiment.

In an embodiment, FIG. 2C shows the user interface 204 remotely located. The user interface 204 is a remote device aiding remote access to the drug dispenser 202. The user interface 204 may also include an application programming interface and a web application connected with the input interface 205 as the mobile devices and computers have a biometric sensor for biometric information of the user. The application programming interface and a web application may also have a unique identity to be set for allowing to dispense the drug from the drug dispenser. The processor 210 is configured to be in communication with the input interface 205 through the communication module 230 which facilitates communication with the server and the drug dispenser 202.

In an embodiment, the input interface 205, the output interface 208, the processor 210, and the memory 212 are added or retrofitted to existing drug dispenser 202 to add access control to the drug dispenser. In some applications, drug dispenser 202 may include the user interface 204, the processor 210, and the memory 212 are in the original manufacture or assembly.

In an embodiment, the input interface 205 is inside a remote device aiding remote access to the drug dispenser 202. The authentication of the user may also include authentication through an application programming interface and a web application connected with the authentication sensor, as the mobile devices and computers have a biometric sensor for a biometric information of the user. The application programming interface and a web application may also have a unique identity to be set for the dispensing of the drug from the drug dispenser. The processor 210 is configured to be in communication with the input interface 205 through the communication module 230 which facilitates communication with the server and the drug dispenser 202. The communication module 230 comprises any suitable wireless technology such as cellular which can include, but is not limited to, Global System for Mobile communication, Code Division Multiple Access, Wireless in Local Loop, General Packet Radio Services, or it can also utilize Low Power Wide Area Networks (LPWANs) such as Bluetooth, Bluetooth low energy, Wi-Fi, Z-Wave, Thread and Zigbee. Z-Wave is a wireless communication protocol used primarily in smart home networks, allowing smart devices to connect and exchange control commands and data with each other.

In an embodiment, the communication module 230 may comprise a wired connection such as LAN, WLAN and WAN.

In an embodiment, the processor 210 is configured to receive through the input interface 205, a unique identity, and a biometric information of a user through the authentication sensor 206. The authentication sensor 206 is at least one of a fingerprint scanner, a facial recognition system (i.e., a camera with corresponding facial recognition software), an iris scanner, and a retinal scanner. In still further embodiments, the authentication sensor may be any other type of biometric sensor now known or later developed.

In an embodiment, the input interface 205 may receive the unique identity of the user comprising at least one of a unique identification number, an RFID tag, a password, and an unlocking pattern.

In an embodiment, the drug dispenser is actuated by a second level of authentication. The second level of authentication comprises a unique identity and biometric information. In the first case of the second level of authentication the patient's biometric information is received through the authentication sensor and the practitioner enters the unique identity. In the case of only the patient's second level of authentication, the unique identity and the biometric information of a patient is received. In the case of only the practitioner's second level of authentication, the unique identity and the biometric information of a practitioner is received.

In an embodiment, the processor 210 is configured to interact with the server to authenticate the user by matching credentials of the unique identity against a record of practitioners and a record of patients stored in the database. The processor 210 is configured to interact with the server to authenticate the user by matching credentials of the biometric information against a record of practitioners and a record of patients stored in the database. The record of patient comprises a name of patient, age of the patient, gender of the patient, a disease, a type of treatment going on, symptoms of the disease, other diseases, allergies, biometric information, unique identity information, physiological information, biological marker of patient, drug prescription, scheduled timings to take the drug. The record of practitioner comprises name of practitioner, age of practitioner, gender of the patient, qualification of the practitioner, experience in years, biometric information, unique identity information, name of patient under the practitioner's supervision. The biometric information and the unique identity of the user is pre-stored in the database for the matching of credentials. The biometric information and the unique identity are stored in the database when the user registers himself for the first time in the system. The system may ask for registration for a first-time user, the registration of the patient comprises name of patient, age of the patient, gender of the patient, a disease, a type of treatment going on, symptoms of the disease, other diseases, allergies, biometric information, unique identity information, physiological information, biological marker of patient, drug prescription, scheduled timings to take the drug. The registration of a practitioner comprises name of practitioner, age of practitioner, gender of the patient, qualification of the practitioner, experience in years, biometric information, unique identity information, name of patient under the practitioner's supervision. The registration of the user may only be done by the authorized owner of the system. The prescription is received through the user interface.

In an embodiment, the prescription is received from a digital medium and as a blockchain token. The digital medium comprises a message, and an email. The processor interacts with the server to check a drug name, a last dispensing time, a dosage time, a quantity of the drug delivered to the user in a day, quantity of the drug accessed by the user in the day before dispensing the drug to the user. The quantity of the drug dispensed is in milligrams and milliliters. The drug comprises a controlled substance, an opioid, a narcotic drug, and a psychedelic drug.

In an embodiment, if the user is new, the user is required to properly register a new user account with the system 200 via the user interface 204—or, alternatively, via any other computing or electronic device capable of communicating with the system 200. As part of the registration process, the patient is asked to provide select details related to at least one of the patient's personal information, as well as a unique identity and at least one biometric marker associated with the user such as a fingerprint, a facial image, a retinal image, or an iris image, for example. In at least one embodiment, the user is also provided with the at least one prescription, which is then associated with the drug dispenser 202 for enabling selective communication, as discussed further below. In at least one embodiment, the drug containers are loaded into the drug storage, or the drug storage is connected to the drug dispenser 202 by a conveying mechanism. The system is configured to receive a prescription. If the drug containers are associated with a new prescription, the user requires the patient (or the practitioner) to register the prescription with the system.

In at least one such embodiment, the user is able to register the prescription by scanning or inputting a unique prescription code into the user interface 204 through a scanner 107, with the prescription code containing the necessary information related to the prescription distribution, including a dosage interval (i.e., the amount of time between distributing the drug containers) and a dosage quantity (i.e., the quantity of drug to be distributed at each dosage interval). In at least one such embodiment, the patient is able to register the prescription by scanning a visual barcode (such as a Quick Response (QR) code, for example) using a scanner 107 of the user interface 104.

In at least one embodiment, the processor 210 encrypts each of the biometric information, unique identity, and prescription code with a unique hash value (such as a random number, in at least one embodiment) to be stored in the corresponding database of the user, thereby creating a unique link. In this way, based on the user's unique identity, biometric information and prescription code prevents anyone else from accessing the drug container from the drug dispenser 202.

In at least one embodiment, after the prescription has been registered with the system 200, the system 200 provides a countdown timer or otherwise notes the date and time for the next dosage based on the associated dosage interval of the user in the database via the display screen of the output interface 208. Upon determining that the next dosage is available for the user, the system 200 notifies the user using at least one of an audible, visual and/or vibrational alert via the output interface 208.

In at least one embodiment, the patient is required to provide the appropriate biometric information via the authentication sensor and also input their unique identity via the input interface 205. In at least one such embodiment, the user must provide the appropriate biometric information within a finite, pre-defined period of time—such as within five minutes from the system 200 notifying the patient of the dosage availability, for example—else the drug container will not be dispensed to the user for that dosage interval. Additionally, in at least one such embodiment, the user must input their unique identity within a finite, pre-defined period of time—such as within one minute from the user providing the appropriate biometric information, for example—else the drug or the drug container will not be dispensed to the user for that dosage interval. Additionally, in at least one such embodiment, the system 200 requires the user to provide the appropriate biometric information and unique identity in sequence. Upon the system 200 authenticating the provided biometric information and unique identity, the processor 210 actuates the actuating mechanism to dispense the drug container equal to the associated dosage quantity in the prescription via the outlet of the drug dispenser 202. In at least one embodiment, the drug dispenser 202 may only dispense the quantity of drug container after the user activates the actuator of the drug dispenser by user authentication and prescription verification. In at least one such embodiment, the actuator is activated within a finite, pre-defined period of time—such as within five minutes from the system authenticating the user, for example—else the drug containers may not be dispensed to the user for that dosage interval. After dispensing the drug container from the drug dispenser to the user, the system 200 schedules the next dosage based on the associated dosage interval. In at least one embodiment, the system 200 also records the date, time, and dosage quantity, which can be subsequently reviewed by the patient or an authorized official. In at least one such embodiment, the system 200 utilizes blockchain to securely store this data, so as to maintain a tamper-proof record that may be reviewed by the authorized clinician. In at least one embodiment, if the user attempts to obtain the drug container during any time other than the scheduled dosage times, the system alerts the user that they must wait until the next scheduled dosage time.

In at least one embodiment, upon the system 200 determining that the at least one drug storage connected to the drug dispenser 202 is empty or running low, the system 200 notifies the authorized owner that a new prescription or alternatively, a refill is required.

Figure 3:
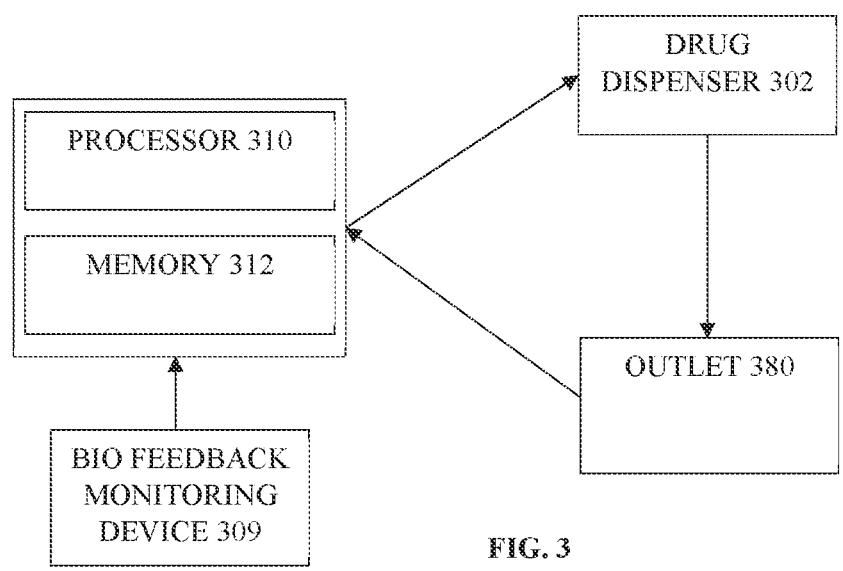
FIG. 3 shows a block diagram of an embodiment of the drug dispenser having a biofeedback monitoring device.

In an embodiment, FIG. 3 shows the system comprising a biofeedback monitoring device 309. The biofeedback monitoring device 309 receives at least one vital of the patient to whom the drug is to be delivered. The at least one vital of the user comprises at least one of a pupil dilation of the user, a breathing rate of the user, a heart rate of the user and a blood pressure of the user. The at least one vital of the user is registered in the database during registration of the user. The registration of the user comprises: a name, a gender, an age, a disease, a type of treatment going on, a symptom of the disease, other ailment, an allergy related information, the biometric information, unique id information, a range of values of at least one vital of the user, physiological information, biological marker of user, drug prescription, a scheduled time to take the drug. The at least one vital received by the system is monitored by comparing it with a range of values of the at least one vital of the user in the database. The system comprises an alarm to generate an alert through the alarm to notify the practitioner if the at least one vital of the user monitored is abnormal. The at least one vital is abnormal if the at least one vital received by the system is not within the range of values of the at least one vital of the user in the database. The drug dispenser is locked for further dispensing if the at least one vital of the user monitored is abnormal. The output of the bio-feedback monitoring device 209 controls a quantity of drug dispensed from the drug dispenser. The range of vitals for each patient is stored separately in the database. After receiving the identity of the user, the vitals of the user are received. So, the vitals of a particular user are compared with the vitals of that particular user in the database and the quantity of drug to be dispensed is then decided by the processor by analyzing the output of the biofeedback monitoring device. As an example, an identity of a patient XYZ is authenticated and vitals of the patient XYZ are received. The processor searches for the corresponding vitals of the patient XYZ in the database and compares the received values of the vitals and controls the quantity of the drug to be dispensed.

In at least one embodiment, as illustrated in the simplified schematic view of FIG. 3, the system 300 also provides at least one biofeedback monitoring device 309 in communication with the processor 310 and configured for assisting the system 300 with monitoring one or more vitals associated with the patient, in order to better manage the dispensing of the drug to the user. Opioid use can lead to death due to the effects of opioids on the part of the brain which regulates breathing. An opioid overdose can be identified by a combination of three signs and symptoms pinpointing pupils i.e., pupil dilation; unconsciousness; and difficulties with breathing.

In at least one such embodiment, the biofeedback monitoring device 309 is a respiratory monitor positioned and configured for assisting the system 300 with monitoring a breathing rate of the patient, utilizing acoustic respiratory monitoring or impedance respiratory monitoring, for example. In further embodiments, the biofeedback monitoring device may include any other type of device, sensor, or combination thereof—now known or later developed—capable of substantially carrying out the functionality described herein. In at least one embodiment, the patient device and the at least one monitoring device are one and the same—as such, it is intended that those terms as used herein are to be interchangeable with one another. The biofeedback monitoring device may be a handheld device or a wearable device that can monitor the vitals of the patient.

In at least one such embodiment, the biofeedback monitoring device 309 is an iris scanner positioned and configured for assisting the system 300 with monitoring the pupil dilation of the patient.

In at least one embodiment, in case the at least one monitored vital falls below or rises above a predefined vital threshold—i.e., if the at least one monitored vital is determined to be abnormal—the system 300 attempts to notify the practitioner using at least one of an audible, visual and/or vibrational alert via the output interface 308 for a potential overdose. Additionally, in at least one embodiment, if the patient fails to timely respond to the notification via the user interface 304, depending on the degree of abnormality in the at least one monitored vital (for example, where the biofeedback monitoring device 309 determines that the patient is not breathing—the system 300 automatically alerts local emergency personnel and provides the patient's current location based on the GPS location of the biofeedback monitoring device 309. Additionally, in at least one embodiment, upon the biofeedback monitoring device 309 determining that the at least one monitored vital is abnormal, the processor may temporarily suspend future dispensing of the drug containers until the at least one monitored vital returns to normal. In this way, the biofeedback monitoring device 309 is able to monitor the effects of the drug consumption by the patient and automatically respond accordingly. Similarly, in at least one embodiment, upon processor 310 determining that the patient is not properly using the biofeedback monitoring device 309—for example, if the user is not wearing the biofeedback monitoring device 309 in the proper position, or not wearing the biofeedback monitoring device 309 at all—the processor 310 attempts to notify the patient and the authorized practitioner using at least one of an audible, visual and/or vibrational alert via the output interface 307 and may also temporarily suspend future dispensing of the drug from the drug dispenser until the patient begins using the biofeedback monitoring device 309 properly.

Additionally, in at least one embodiment, upon the biofeedback monitoring device 309 determining that the at least one monitored vital is abnormal, the processor may check the registered values of the vitals for that particular patient in the database of patients. The processor 310, on checking the values of vitals in the database, determines a quantity of the drug to be dispensed, thereby controlling the drug dispensing through the drug dispenser 302. For example, for a patient Z, the respiratory SpO2 value is 97 out of 100. After receiving the value of the vital of the patient Z from the biofeedback monitoring device 309, the processor compares the received value with the stored value that is 97. If for the value 97 the prescribed amount is 10 mg in a dosage, the processor adjusts the quantity of the drug to 7 mg if the received value is 93. The system may utilize predictive analytics using artificial intelligence and machine learning techniques to determine the dosage of drug dispensing depending upon the value of the vitals received by the biofeedback monitoring device 309. The predictive analytics is done using forecast models, outliers' models, or classification models. The classification models are the most simple and easy to use among all other predictive analytics models available. These models arrange the data in categories based on what they learn from the historical data. Classification models provide the solution in "yes" and "no" to provide a comprehensive analysis. The forecast model of predictive analytics involves the metric value prediction for analyzing future outcomes. The model can analyze the unusual data either by itself or by combining it with other categories and numbers present. The most important advantage of the forecast predictive model is that it also considers multiple input parameters simultaneously. This predictive analytics model helps for estimating the numeric value of new data based on historical data. Unlike the classification and forecast model, which works on the historical data, the outlier's model of predictive analytics considers the anomalous data entries from the given dataset for predicting future outcomes. The quantity of the drug, once determined, is then dispensed by the drug dispenser 202. The quantity of the drug dispensed is in milligrams or milliliters.

The processor 310 is configured to actuate the actuating mechanism of the drug dispenser 302 to allow the dispensing of the drug and for the user to access the drug container from the drug dispenser 302. In an embodiment the actuator is a button. However, in alternative embodiments, the actuator may be any other mechanism or combination of mechanisms, now known or later developed, capable of mechanically or electrically causing the drug or drug container to be ejected from the drug dispenser 302 through the outlet 380. The dispensing of the drug container from the drug dispenser 302 is monitored by the camera. The camera could also be attached to the drug dispenser 302 and a picture of the drug container being dispensed is transferred to the processor 310 and compared to the record in a prescription detail in the database to ensure that the drug container dispensed is the correct drug that has been directed to be dispensed to the user. In case of a wrong drug container dispensed, the camera captures the image of the drug as well as the user, and the processor 310 is configured to raise an alarm to notify the practitioners and the authorized owners of the system for a misuse or illegal access of the drug container.

The dispensing of the drug container in the drug dispenser 302 is synchronized with the scheduled time for the dispensing of the drug for a user. After receiving the user information through the authentication sensor, vitals from the biofeedback monitoring device and the prescription through the input interface, and the scheduled time to dispense the drug container for the user are also checked. The drug is dispensed from the drug dispenser only if the time of dispensing of the drug container is the scheduled time for the dispensing of the drug container for the user. The system would not allow the dispensing of the drug container to the user if the scheduled time for the dispensing does not match with the time in real time. In case the scheduled time for the dispensing of the drug container does not match with the time in real time, the system raises an alarm to notify the practitioners and the authorized owners of the system for a misuse or illegal dispensing of the drug.

In an embodiment, the dispensing of the drug container from the drug dispenser 302 is locked for further dispensing if the credentials of the biometric information and the unique identity do not match with the record of practitioners and the record of patients in the database. An authorized owner of the system is able to unlock the drug dispenser 302. The user has a predefined number of the drug containers in a day. If the number of dispensing of the drug container is exceeded in a day for a particular user and if a request to dispense the drug container is received other than a scheduled time, then the dispensing the drug container from the drug dispense 302 is locked by locking the actuator.

In an embodiment, the drug comprises at least one of a controlled substance, an opioid, a narcotic drug, and a psychedelic drug.

In an embodiment, the output interface comprises a display screen. The display screen may be a liquid crystal display (LCD), an e-paper/e-ink display, or an organic LED (OLED) display, or other displays as known to one skilled in the art. The display screen may function to provide usage instructions to the patient, as well as alerts, such as time to take a medication, expiration of a medication, warnings, etc. The display screen may also be equipped with a touch sensitive interface that enables user interaction between the smart dispensing system and the patient. For example, the patient/user can input information related to a scanned medication by way of the touch interface when prompted on the display screen. In one embodiment, a second display screen may be placed on an outer surface of the drug dispenser 202. This second display screen can be a high-density color LCD display capable of displaying a color image of the medication, e.g., a pill, that the patient is scheduled to take, so that the patient can be assured that he is taking the correct pill. For example, the patient is notified that it is time to take medication. The slot containing the medication due to be taken is illuminated or otherwise indicated. The patient removes the bottle of medication and removes one of the pills, and the image of the pill is displayed on the color LCD screen. The patient is directed to compare the pill in hand with the pill on the screen to assure it is the same pill. The direction to the patient can be given audibly and/or visually on the display screen.

In an embodiment, an RFID location tracking system with real-time data on the status and movement of drug containers is used. Such technology is built on active RFID technology. Active RFID location tracking systems allow tracking the real-time movement of drug containers throughout a monitored area. The system may track RFID tags from afar with the highest accuracy. This data is sent along with the location signal to the RFID reader. Active RFID location tracking uses powered tags, which contain an internal battery. This energy source allows the tag to send out a strong, continuous signal that an RFID reader can pick up. Most RFID tags have batteries that can provide power for weeks or months before needing to be recharged. The information picked up by an RFID reader is sent to a computer containing RFID location tracking system software. It interprets the data and displays it on the dashboard as a moving image on an overlay of the building map. With the map screen open, the signals from active ID tags ping off locators throughout the monitored area. These active RFID tags will be shown moving second-by-second around the monitored area.

In an embodiment, the drug container comprises the indicator tag comprising at least one of a RFID tag, Universal Product Code indicia, a Quick Response code, a high-capacity color barcode, and an unpowered near-field communication tag on a casing of the drug in order to trace the drug. The indicator tag may be placed on the covering of the drug. When the drug storage for the dispenser is refilled, the drug container that is to be stored in the container 220 is assigned a new indicator tag on each drug container stored in the drug storage. The indicator tag comprises a detail of the drug comprising an inventory number of the drug, a name of the drug, an expiry date, and a disease it is used to treat. The indicator tag is scanned by a scanner. The first sensor comprises a scanner to scan the Universal Product Code indicia, the Quick Response code, the high-capacity color barcode, and the unpowered near-field communication tag. The information of the drug is stored on the indicator tag. The information of the drug is stored in the database through the scanner for the first time when the indicator tag is assigned to each drug. When the drug container is dispensed from the drug dispenser, the scanner reads the information of the drug container dispensed. The information of the drug container dispensed is checked with the information of the drug container stored in the database, the prescription quantity, and the scheduled time. If the quantity of the drug container dispensed is more than the prescription quantity or the dispensing of the drug containers is not on the scheduled time, then the alarm is raised to notify the authorized owner of the system and the practitioner who is supervising the patient for a potential misuse of the drug.

The processor 310 may indicate a time to dispense the drug by referring to inputted information by the patient/user or based on known interactions with other prescribed medications under the system. For example, if medication A and medication B should not be taken together, the processor 310 adjusts the scheduled time accordingly. In one embodiment, time can be tracked by a clock circuit. Moreover, the processor may adjust the scheduled time according to the schedule of the patient so that a patient is not alerted to access the drug container during pre-set sleep hours, for example between 11 PM and 8 AM, or other time intervals set by the patient. The patient may set his own sleep hours by the input interface.

In an embodiment, if the user forgets to access the dispensed drug container at the scheduled time, the user is notified by a notification means such as a buzzer or short-range wireless communication provided by a wireless communication circuit, such as Bluetooth, in communication with a paired bracelet, e.g., wrist alert, or fob, which can be worn, for example, as a pendant. In one embodiment, the notification can occur when the bracelet or pendant lights up and/or vibrates. Other notification means can also be used.

The processor 310 may provide further instructions, such as instructing the patient to take a certain number of pills or amount of liquid medication, to take the medication with food, or refrain from eating for a period after taking the medication. The instructions can be provided via the speaker and/or the display screen.

In one embodiment, the smart dispensing system can be powered by an AC power source or rechargeable battery. A power supply/charging circuit is coupled to the AC power source and the battery. The power supply/charging circuit controls the charging of the rechargeable battery when the system for medical smart storage is plugged into an AC power source. Additionally, the power supply/charging circuit may condition the output power from the AC power source or rechargeable battery to provide appropriate voltages and currents to the various components of the system for medical smart storage. The system for medical smart storage 100 can accept 12V, 110V, 220V power input, but is not limited to this. Whenever any external power sources are available, the system for medical smart storage may be powered by this available external source and in addition the internal rechargeable battery can charge, such as a Lithium-Ion battery. If external power is lost, there can be a seamless switch over to the internal battery, and when external power is restored there can be a seamless switchover back to the external power and the internal battery can begin charging.

In an embodiment, a log of record of dispensing of the drug container is stored in the database by the system through the communication module. The log of record of the dispensing comprises: a name of drug, a time, a date, a day, a month, a year, a quantity of the drug container dispensed, name of the user receiving the drug container, and a quantity of drug containers remaining. As mentioned above, the smart dispensing system may have one or more databases. In one embodiment, one database includes only data from current medication management, such as data obtained when scanning the drug container, such as name of medication, name of manufacturer of medication, image of the medication, dosage instructions, administration instructions, e.g., dosage, administration time, storage instructions, expiration date, remaining refills, interaction data, special instructions, etc., and data indicating in which receptacle the original medication container resides. One or more additional databases comprises information regarding patient data for the user of the system, data regarding medication interactions, compliance information, etc. In one embodiment, one database comprises all of the data and information for the patient, the medications, compliance, prescribing physician/practitioner, etc. In one embodiment, the database can comprise at least a list of the drug the patient is receiving along with the dosage of that medication. Using the smart dispensing system, patient compliance can be monitored to assure the patient is adhering to the proper drug frequency, and this monitoring information can be stored in the database.

In an embodiment, the log of record of the dispensing is encrypted by the system before communicating the log of record of dispensing to the database.

In an embodiment, the log of record of the dispensing of the drug container is stored as a hash value in the database and a ledger of record of the dispensing of the drug container is maintained by the system using blockchain technology. In at least one embodiment, the system encrypts each of the biometric information, unique identity, prescription data and the log of record of the dispensing with a unique hash value (such as a random number, in at least one embodiment) to be stored in the database, thereby creating a unique link there between. In this way, only the associated user according to the biometric information, unique identity, and prescription data is capable of dispensing the drug container from the drug dispenser, which better prevents anyone else from accessing the drug container.

In at least one such embodiment, the system utilizes blockchain to securely store the data and the log of record of dispensing, so as to maintain a tamper-proof record that may be reviewed by the authorized practitioner. In at least one embodiment, if the patient attempts to dispense the drug container during any time other than the scheduled time, the system informs the patient that they must wait until the next scheduled time.

The ledger may be accessible to any medical professional, or drug providing entity that interfaces with the creation of a prescription or dispensation of drugs based on a prescription, including, for example, physicians or other healthcare professionals, doctor's offices, hospitals, pharmacies, mail-order prescription companies or any other company.

In an embodiment, the ledger may be immutable, where, for example, once an entry has been added to the shared ledger system, the entry may not be changed by any party with access to the shared ledger system. As an example, the shared ledger system may be implemented by blockchain technology.

Blockchain technology was developed as a way of providing a publicly transparent and decentralized ledger that is configured to track and store digital transactions in a publicly verifiable, secure, and hardened manner to prevent tampering or revision.

A typical blockchain includes three primary functions: read, write, and validate. For example, a user of the blockchain must have the ability to read the data that resides on the blockchain. A user of the blockchain must also have the ability to write, e.g., append data to the blockchain. Every write operation starts out as a proposed transaction that is posted on the network. The proposed transaction may not always be valid, for example, it may be malformed (syntax errors), or it may constitute an attempt to perform a task for which the submitter is not authorized. Validation refers to filtering out invalid transactions and then deciding on the exact order for the remaining, valid, transactions to be appended to the blockchain as part of a new block.

Once ordered, the transactions are packaged into a new block, and the new block is voted on by the validator nodes associated with the blockchain to determine whether to add the new block to the blockchain. If a consensus to add the new block is reached, e.g., a threshold number of "for" votes, the new block may be appended to the blockchain. Each new block that is appended to the blockchain also includes a hash of the previous block. Accordingly, as each new block is added, the security and integrity of the entire blockchain is further enhanced. It is important to note that once data is written to the blockchain, for example, once a block including a set of transactions has been appended to the blockchain, that data can no longer be altered or modified. In a typical blockchain, the anonymity of the users is protected through the use of pseudonyms and the transaction data itself is protected through the use of cryptography, e.g., via the use of hash codes.

In an embodiment, a blockchain includes a plurality of data blocks. Each data block is a data structure that includes data representing transactions, for example, log of record of the dispensing of drug prescriptions, queries to the blockchain regarding a prescription, or any other transaction related to a prescription. As described above, as new transactions are submitted to the blockchain and validated by validator nodes, additional data blocks are generated by the validator nodes and appended to the blockchain. Each new data block includes a set of validated transactions and a hash of the content of the immediately previous data block. For example, data block "2" includes a hash of the content of block "1", block "n" includes a hash of the content of block "n–1", etc. Some non-limiting examples of blockchains include Bitcoin®, Ethereum®, Open Ledger™ or other similar blockchains. In an embodiment, the hashes may be generated by the validator nodes as the validator nodes generate new blocks for addition to the blockchain.

In an embodiment, blockchain is stored in a decentralized manner on a plurality of nodes, e.g., computing devices located in one or more networks. Nodes may each include a memory that stores at least a portion of a blockchain ledger. Ledger includes any data blocks that have been validated and added to the blockchain. In an embodiment, every node may store the entire ledger. In an embodiment, each node may store a portion of the ledger. In an embodiment, some, or all of a blockchain may be stored in a centralized manner. Nodes may communicate with one another via communication modules, e.g., wired, or wireless connections, over the internet, etc. to transmit and receive data related to the ledger. For example, as new data blocks are added to the ledger, nodes may communicate or share the new data blocks via a communication module. In an embodiment, some or all of nodes may be operated by a health configuration such as a group of healthcare providers, a pharmacy, a group of pharmacies, an insurance provider, a group of insurance providers, or any other entity that may have a stake in monitoring prescription usage and the log of record of dispensing to the drug container. In an embodiment, some or all of the nodes may be anonymous and unrelated to the creators or users of the prescription.

In an embodiment, any transactions submitted to the blockchain are validated by a set of validator nodes associated with the blockchain. For example, transactions may be transmitted to one or more of the validator nodes and may be shared between the validator nodes for validation and consensus. Each validator node determines whether a transaction is valid and whether the transaction complies with the rules of the blockchain. The validator node adds a plurality of the validated transactions to a data block and submits the data block for consensus by all or some of the other validator nodes. The other validator nodes then vote "for" or "against" appending the data block containing the transactions to the blockchain. A consensus of the set of validator nodes, e.g., a threshold number of identical votes "for" or "against," is required to allow or deny the data block to be appended to the blockchain. In an embodiment, one or more of the nodes may also be validator nodes. In an embodiment, nodes that are not validator nodes may perform processing such as, for example, receiving transaction submissions, providing member services, handling application programming interface (API) requests from users, or other similar functions. In this manner, the processing power of the validator nodes may be preserved for generating new blocks, reaching consensus, and monitoring the other validator nodes. Validator nodes may communicate with one another via communication modules, e.g., wired, or wireless connections, over the internet, etc., to transmit and receive data. For example, as new data blocks are generated by validator nodes, validator nodes may communicate or share the new data blocks and transmit and receive consensus messages via a communication module. In an embodiment, some or all validator nodes may be operated by a healthcare provider, a group of healthcare providers, a pharmacy, a group of pharmacies, an insurance provider, a group of insurance providers, or any other entity that may have a stake in monitoring prescription usage. In an embodiment, some or all validator nodes may be anonymous and unrelated to the creators or users of the prescription.

In an embodiment, the users of the ledger may be known and may provide contact information such that when new transactions or queries related to a particular prescription are received from a new user, e.g., a pharmacy, the new user may easily identify the prior user, e.g., physician or other medical personnel, and may contact the prior user when a potential case of fraud or drug abuse is detected.

In an aspect, any prescription related activities may be tracked and logged as transactions for appending to the blockchain implementing the ledger in the blockchain. For example, the creation of a new prescription by a physician or other healthcare professional, the modification of a prescription by the physician or other healthcare professional, the dispensing of the drug container by the user, queries to the ledger about a prescription by a physician, other healthcare professional, pharmacy, or other entity, or other similar transactions or activities related to a prescription may be appended to the ledger.

In an embodiment, the validation code may be generated by a shared ledger system at a time when the prescription data is submitted to the prescription details in the database, e.g., via network interfaces, as a transaction for addition to the blockchain. For example, one or more nodes or validator nodes may generate the validation code when the prescription data is received from a prescription entry device and may add the validation code to the prescription data prior to appending the prescription data to a block for addition to the blockchain.

Once prescription data for a prescription has been submitted to a shared ledger system and a validation code has been generated and added to the prescription data, prescription data may be validated and be added to a new block by a validator node of the shared ledger system. The validators may then reach a consensus and add the new block containing the prescription data to the blockchain. In an embodiment, only prescriptions received from verified prescribers, e.g., those using prescription entry devices, may be validated for addition to the blockchain. For example, if a prescription is received from a non-verified device, the shared ledger system may deny entry of the prescription to the blockchain. In an embodiment, all or part of the prescription data may be encrypted by a prescription entry device or by a shared ledger system when submitted for addition to the blockchain to protect patient privacy. In an embodiment, an image of the prescription may be stored separately from the blockchain, for example, in a separate database, and the prescription data stored on the blockchain may include a link, e.g., a URL link, pointing to the prescription image.

In an embodiment, prescription data may be checked against other prescriptions already added to the blockchain. For example, the validator node may determine whether there is already an active prescription for the listed patient for the same medication. If such a prescription exists, the shared ledger system may notify the prescribing physician to manually verify the existence of the prior active prescription. For example, the prior active prescription that is already appended to the blockchain may include identification or contact information for a prescribing physician that may be used to verify whether the patient has already received a prescription for the same medication from another physician. This verification may be used to prevent doctor shopping where, for example, a patient may receive separate prescriptions for the same medication from more than one physician.

In an embodiment, the log of record of the dispensing is viewable on a dashboard. The log of record of the dispensing is accessible to a plurality of officials. The log of record of the dispensing is accessible to an authorized third-party official for unbiased monitoring.

In an embodiment, the communication through the communication module is secured by the cyber security module.

In an embodiment, the cyber security module further comprises an information security management module providing isolation between the input interface, output interface, the processor, the server, the database, and the communication module.

In an embodiment, the system is a Drug Enforcement Administration compliant system. The DEA was established in 1973 as the federal organization in charge of enforcing the controlled substances laws of the United States. The mission of the Drug Enforcement Administration (DEA) is to enforce the controlled substances laws and regulations of the United States and bring to the criminal and civil justice system of the United States, or any other competent jurisdiction, those organizations and principal members of organizations involved in the growing, manufacture, or distribution of controlled substances appearing in or destined for illicit traffic in the United States; and to recommend and support non-enforcement programs aimed at reducing the availability of illicit controlled substances on the domestic and international markets. The relevant Drug Enforcement Administration requirements for controlled substances storage are found in 21 CFR 1301.72 of the Food and Drug Administration. In summary form, they mandate: Where small quantities permit, a safe or steel cabinet. Walls of the vault and ceilings of reinforced concrete or "substantial" masonry. Vault doors and frames provide 30 "man minutes" against surreptitious entry, up to 20 "man hours" against lock manipulation. Vault doors outfitted with day gates that are self-closing and self-locking. Alarms, and monitoring devices such as sound accumulators or ultrasonics. Cages with walls of not less than No. 10 gauge steel fabric, mounted on steel posts set in concrete or installed with pinned or brazed lab bolts; with mesh openings not more than 2.5 in. Cage ceilings with similar construction (lighter gauge steel mesh in some situations), or cages that are secured to the ceiling of the storage facility. Self-closing and self-locking doors for cages; alternatively, for occasional access to the cage, a 24-hour/day monitoring service.

Figure 4A:
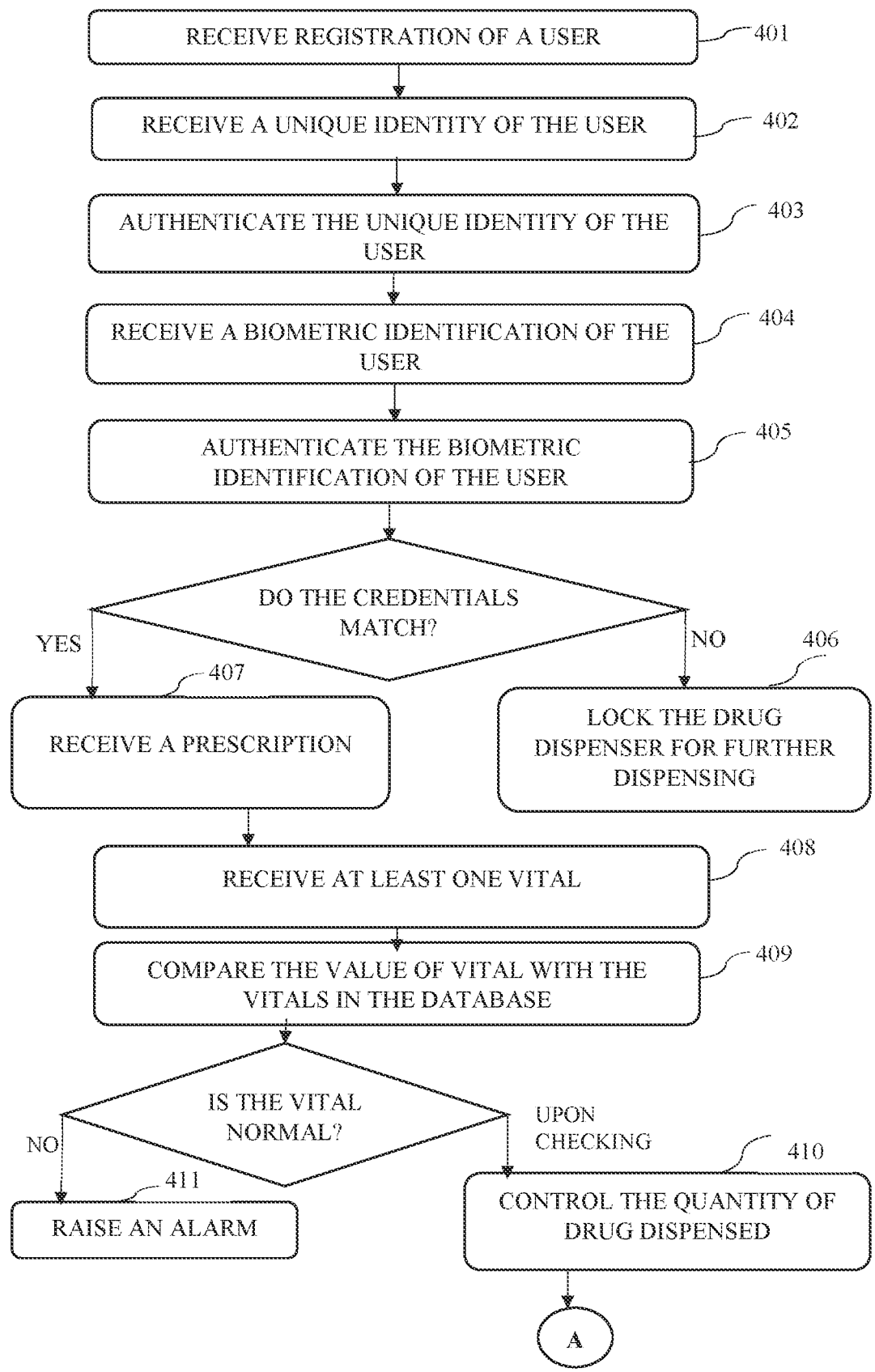
FIG. 4A shows a method for smart dispensing.
Figure 4B:
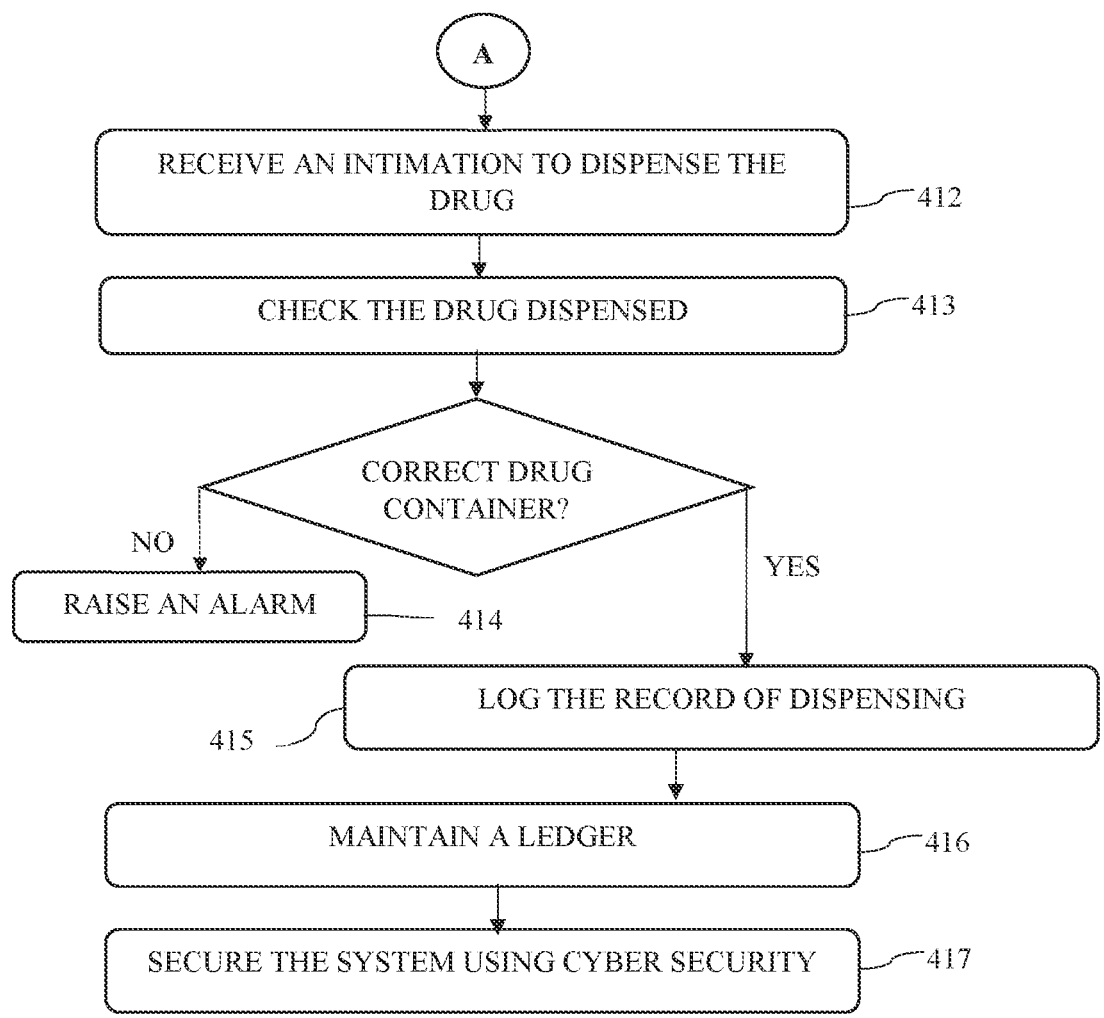
FIG. 4B shows the continuation of the method for smart dispensing.

FIGS. 4A and 4B illustrates a method for smart drug dispensing.

At step 401, the user is registered into the system in order to allow the dispensing of the drug container from the drug dispenser and to authorize the user to access the drug container that is dispensed from the drug dispenser. The biometric information and the unique identity of the user is pre-stored in the database for the matching of credentials. The one or more vitals of a patient are also pre-stored in the database. The one or more vitals comprises at least one of a pupil dilation of the user, a breathing rate of the user, a heart rate of the user and a blood pressure of the user. The biometric information, the unique identity, the one or more vitals of the user are stored in the database when the user registers himself for the first time in the system. The system may ask for registration for a first-time user, the registration of the patient comprises name of patient, age of the patient, gender of the patient, a disease, a type of treatment going on, symptoms of the disease, other diseases, allergies, biometric information, unique identity information, physiological information, biological marker of patient, drug prescription, scheduled timings to take the drug. The registration of a practitioner comprises name of practitioner, age of practitioner, gender of the patient, qualification of the practitioner, experience in years, biometric information, unique identity information, name of patient under the practitioner's supervision. The registration of the user may only be done by the authorized owner of the system.

At step 402, the system is configured to receive the unique identity of the user when a user needs the drug container from the drug dispensing system. The unique identity of the user comprises a unique identification number, an RFID tag, a password, and an unlocking pattern.

At step 403, the system interacts with the server to authenticate the user by matching credentials of the unique identity against a record of practitioners and a record of patients stored in the database. The record of patient comprises a name of patient, age of the patient, gender of the patient, a disease, a type of treatment going on, symptoms of the disease, other diseases, allergies, biometric information, unique identity information, physiological information, biological marker of patient, drug prescription, scheduled timings to take the drug. The record of practitioner comprises name of practitioner, age of practitioner, gender of the practitioner, qualification of the practitioner, experience in years, biometric information, unique identity information, name of patient under the practitioner's supervision.

At step 404, the system receives biometric information of the user. The biometric information received comprises a fingerprint, a facial recognition (i.e., a camera with corresponding facial recognition software), an iris scan, and a retinal scan. In still further embodiments, the biometric information may be any other type of biometric sensor now known or later developed.

At step 405, the system interacts with the server to authenticate the user by matching credentials of the biometric information against a record of practitioners and a record of patients stored in the database. The biometric information and the unique identity of the user is pre-stored in the database for the matching of credentials. The biometric information and the unique identity are stored in the database when the user registers himself for the first time in the system.

At step 406, in case any one of the or both the credentials of the biometric information and the unique identity do not match with the record of practitioners and the record of patients in the database, the drug dispenser is locked for further dispensing. The user has a predefined number of dispensing to the drug container in a day. If the limit of dispensing is reached in a day and if a request to dispense the drug container is received other than a scheduled time, then the drug dispenser is locked for further dispensing.

At step 407, receive a prescription.

At step 408, receive at least one vital of a user as an input to a bio-feedback monitoring device.

At step 409, compare the value of vitals received with the range of values of the at least one vital of the user in the database.

At step 410, controlling the quantity of the drug to be dispensed from the output of the biofeedback monitoring device.

At step 411, generating an alert through an alarm to notify a practitioner if the at least one vital of the user monitored is abnormal. The at least one vital of the user monitored is abnormal if the at least one vital received by the system is not within the range of values of the at least one vital of the user in the database.

Referring to FIG. 4B, at step 412, the system receives an intimation to dispense the drug container from the drug dispenser.

At step 413, the system checks if the drug container dispensed is the correct drug container and the quantity of the drug containers is the prescribed quantity of the drug containers. The system checks the quantity of drug containers, the scheduled time of delivery of the drug containers, and the prescription quantity of the drug containers by interacting with the database on the server.

At step 414, raise an alarm if the drug container or any of the quantity or the scheduled time to dispense the drug container does not match with the database.

At step 415, a log of record of dispensing of the drug container is stored in the database by the system through the communication module. The log of record of the dispensing comprises: a name of drug, a time, a date, a day, a month, a year, a quantity of the drug container dispensed, name of the user receiving the drug container, and a quantity of drug container remaining.

At step 416, a log of record of the dispensing of the drug container is stored as a hash value in the database and a ledger of record of the dispensing of the drug container is maintained using blockchain technology.

At step 417, log of record of the dispensing of the drug container is secured by cyber security. The data to be communicated between the system and the server is analyzed for potential cyber security threats. The data is encrypted in cases where no cyber security threat is detected. The encrypted data is transmitted to the server or to the system. The data received is checked for a cyber security threat. The data is decrypted when no cyber security threat is detected; else the data is discarded.

Cyber Security Module

According to an embodiment, it is a system comprising, a device; a communication module communicating with a server; a user interface; a bio-feedback monitoring device; a drug dispenser; a database; and a cyber security module.

In an embodiment, the cyber security module further comprises an information security management module providing isolation between the system and the server.

In an embodiment, the information security management module is operable to, receive data from at least one of the user interface, the bio-feedback monitoring device, the drug dispenser, and the database, exchange a security key at a start of the communication between the communication module and the server, receive the security key from the server, authenticate an identity of the server by verifying the security key, analyze the security key for a potential cyber security threat, negotiate an encryption key between the communication module and the server, encrypt the data; and transmit the encrypted data to the server when no cyber security threat is detected.

In an embodiment, the information security management module is operable to exchange a security key at a start of the communication between the communication module and the server, receive the security key from the server, authenticate an identity of the server by verifying the security key, analyze the security key for a potential cyber security threat, negotiate an encryption key between the system and the server, receive encrypted data from the server, decrypt the encrypted data, perform an integrity check of the decrypted data and transmit the decrypted data to at least one of the user interface, the bio-feedback monitoring device, the drug dispenser, and the database through the communication module when no cyber security threat is detected.

In an embodiment, the information security management module is configured to raise an alarm when the cyber security threat is detected.

In an embodiment, the system of claim 4, wherein the information security management module is configured to raise an alarm when the cyber security threat is detected.

In an embodiment, the information security management module is configured to discard the encrypted data received if the integrity check of the encrypted data fails.

In an embodiment, the information security management module is configured to check the integrity of the encrypted data by checking accuracy, consistency, and any possible data loss during the communication through the communication module.

In an embodiment, the information security management module is configured to perform asynchronous authentication and validation of the communication between the communication module and the server.

In an embodiment, a perimeter network provides an extra layer of protection.

In an embodiment, the perimeter network protects the system from a cyber security threat by using a plurality of firewalls.

In an embodiment, the system may comprise a cyber security module, a communication module, a server, and a database.

In one aspect, a secure communication management (SCM) computer device for providing secure data connections in the healthcare environment is provided. The SCM computer device includes a processor in communication with memory. The processor is programmed to receive, from an input interface, a drug storage or a database. The first data message is in a standardized data format. The processor is also programmed to analyze the first data message for potential cyber security threats. If the determination is that the first data message does not contain a cyber security threat, the processor is further programmed to convert the first data message into a first data format associated with the healthcare environment and transmit the converted first data message to the healthcare system using a first communication protocol associated with the healthcare system.

According to an embodiment, secure authentication for data transmissions comprises, provisioning a hardware-based security engine (HSE) located in communications system, said HSE having been manufactured in a secure environment and certified in said secure environment as part of an approved network; performing asynchronous authentication, validation and encryption of data using said HSE, storing user permissions data and connection status data in an access control list used to define allowable data communications paths of said approved network, enabling communications of the communications system with other computing system subjects to said access control list, performing asynchronous validation and encryption of data using security engine including identifying a user device (UD) that incorporates credentials embodied in hardware using a hardware-based module provisioned with one or more security aspects for securing the system, wherein security aspects comprising said hardware-based module communicating with a user of said user device and said HSE.

In an embodiment, there is a cyber security module embedded in each of the layers namely Human Layer, Perimeter Layer, Network Layer, Endpoint Layer, Application Layer, Data Layer, and Mission Critical Layer. Each layer represents a different stage in network communication, from a human typing on a keyboard to the data system used for applications.

Figure 5A:
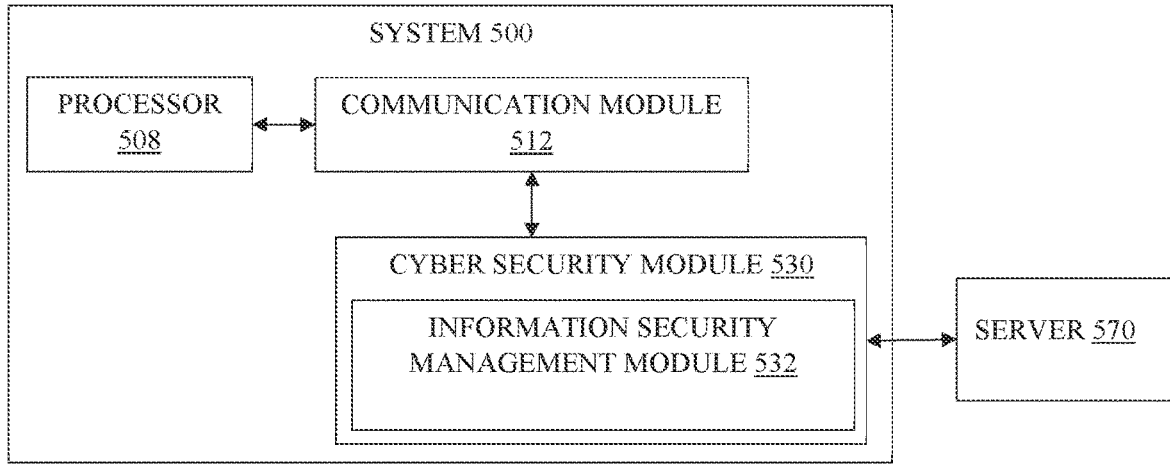
FIG. 5A shows a block diagram of the cyber security module in view of the system and server.

In an embodiment, FIG. 5A shows the block diagram of the cyber security module. The communication of data between the system 500 and the server 570 through the communication module 512 is first verified by the information security management module 532 before being transmitted from the system to the server or from the server to the system. The information security management module is operable to analyze the data for potential cyber security threats, encrypt the data when no cyber security threat is detected, and transmit the data encrypted to the system or the server.

Figure 5B:
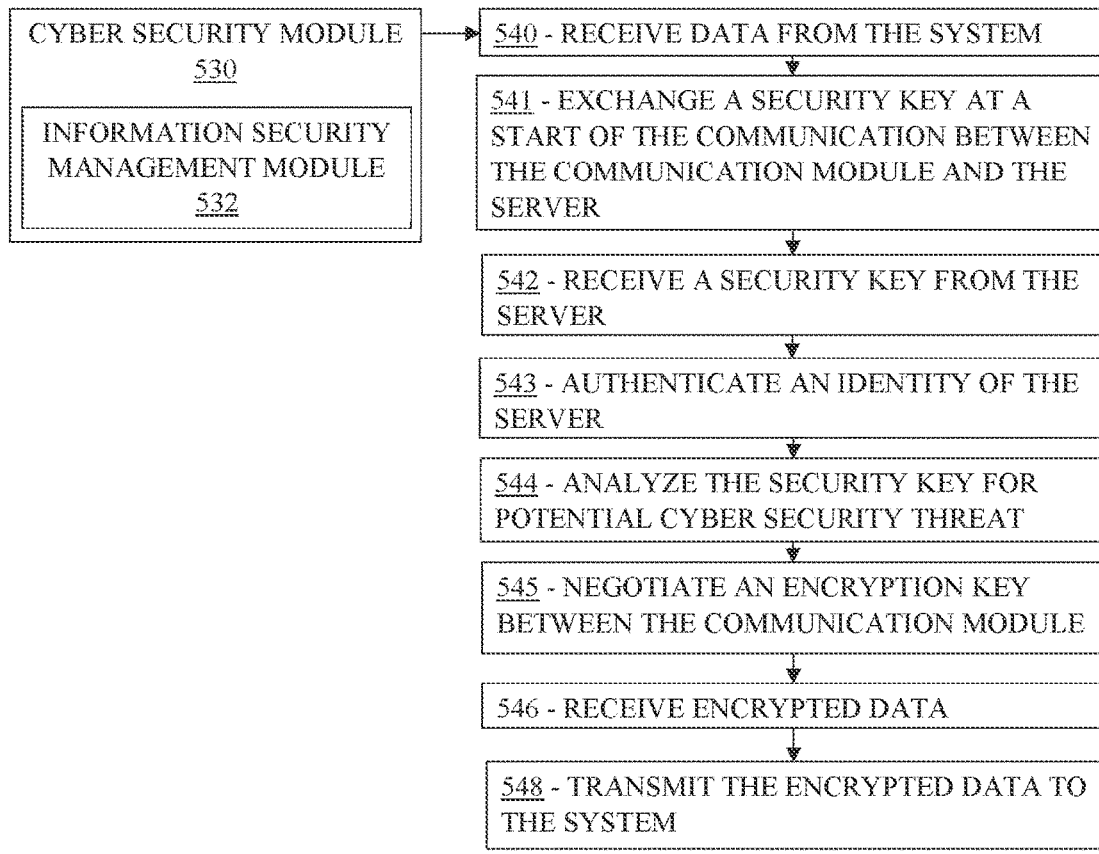
FIG. 5B shows an embodiment of the cyber security module.

In an embodiment, the cyber security module further comprises an information security management module providing isolation between the system and the server. FIG. 5B shows the flowchart of securing the data through the cyber security module 530. At step 540, the information security management module is operable to receive data from the system, for example, at least one of an input interface, the drug storage, and the database. At step 541, the information security management module exchanges a security key at a start of the communication between the communication module and the server. At step 542, the information security management module receives a security key from the server. At step 543, the information security management module authenticates an identity of the server by verifying the security key. At step 544, the information security management module analyzes the security key for potential cyber security threats. At step 45, the information security management module negotiates an encryption key between the communication module and the server. At step 546, the information security management module encrypts the data. At step 547, the information security management module transmits the encrypted data to the server when no cyber security threat is detected.

Figure 5C:
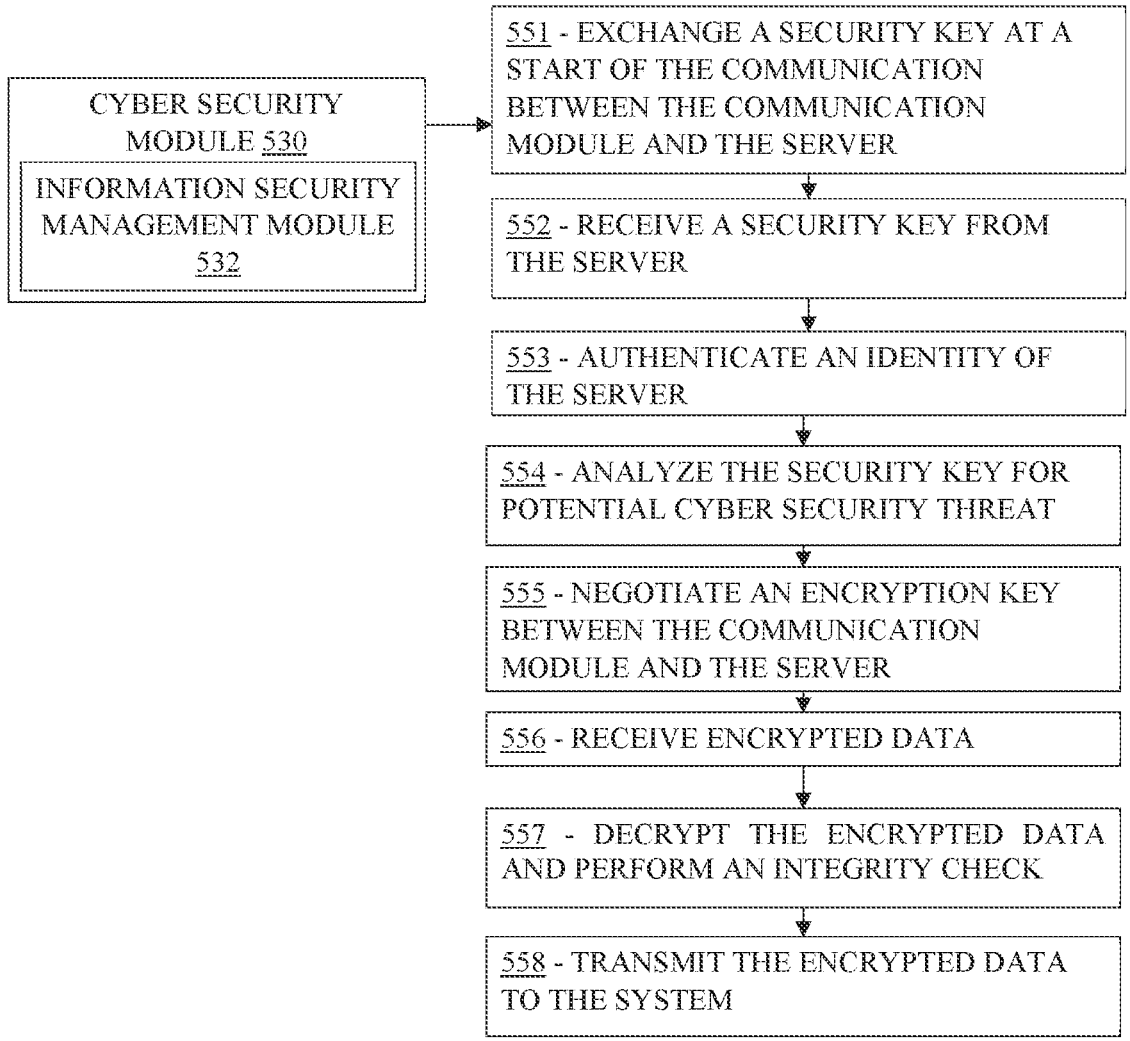
FIG. 5C shows another embodiment of the cyber security module.

In an embodiment, FIG. 5C shows the flowchart of securing the data through the cyber security module 530. At step 551, the information security management module is operable to: exchange a security key at a start of the communication between the communication module and the server. At step 552, the information security management module receives a security key from the server. At step 553, the information security management module authenticates an identity of the server by verifying the security key. At step 554, the information security management module analyzes the security key for potential cyber security threats. At step 555, the information security management module negotiates an encryption key between the system and the server. At step 556, the information security management module receives encrypted data. At step 557, the information security management module decrypts the encrypted data, performs an integrity check of the decrypted data. At step 558, the information security management module transmits the decrypted data to the system, for example, at least one of output interface, drug storage, and the database through the communication module when no cyber security threat is detected.

In an embodiment, the integrity check is a hash-signature verification using a Secure Hash Algorithm 256 (SHA256) or a similar method. A cryptographic hash (sometimes called 'digest') is a kind of 'signature' for a text or a data file. SHA256 generates an almost-unique 256-bit (32-byte) signature for a text.

In an embodiment, the information security management module is configured to perform asynchronous authentication and validation of the communication between the communication module and the server.

In an embodiment, a perimeter network provides an extra layer of protection. In an embodiment, the perimeter network protects the system from a cyber security threat by using a plurality of firewalls. Usually, a perimeter network is the final step a packet takes traversing one of the system's networks on its way to the internet; and conversely the first network encountered by incoming traffic from the Internet to the system.

In an embodiment, a demilitarized zone (DMZ) network functions as a subnetwork containing an organization's exposed, outward-facing services. It acts as the exposed point to an untrusted network, commonly the Internet. A DMZ network will add an extra layer of security to an organization's local area network. It is a protected and monitored network node that faces outside the internal network and can access what is exposed in the DMZ, while the rest of the organization's network is safe behind a firewall. A DMZ Network gives organizations extra protection in detecting and mitigating security breaches before they reach the internal network, where valuable assets are stored. All services accessible to users on communicating from an external network can and should be placed in the DMZ, if one is used. The most common services include, but are not limited to, web servers, mail servers, file transfer protocol (FTP) servers.

In an embodiment, the information security management module is configured to raise an alarm if a cyber security threat is detected. In an embodiment, the information security management module is configured to discard the encrypted data received if the integrity check of the encrypted data fails.

In an embodiment, the information security management module is configured to check the integrity of the encrypted data by checking accuracy, consistency, and any possible data loss during the communication through the communication module.

In an embodiment, the information security management module is configured to perform asynchronous authentication and validation of the communication between the communication module and the server.

In an embodiment, the server is physically isolated from the system through the information security management module. When the system communicates with the server as shown in FIG. 5A, identity authentication is firstly carried out on the system and the server. The system is responsible for communicating/exchanging a public key of the system and a signature of the public key with the server. The public key of the system and the signature of the public key are sent to the information security management module. The information security management module decrypts the signature and verifies whether the decrypted public key is consistent with the received original public key or not. If the decrypted public key is verified, the identity authentication is passed. Similarly, the system and the server carry out identity authentication on the information security management module. After the identity authentication is passed on to the information security management module, the two communication parties, the system, and the server, negotiate an encryption key and an integrity check key for data communication of the two communication parties through the authenticated asymmetric key. A session ID number is transmitted in the identity authentication process, so that the key needs to be bound with the session ID number; when the system sends data to the outside, the information security gateway receives the data through the communication module, performs integrity authentication on the data, then encrypts the data through a negotiated secret key, and finally transmits the data to the server through the communication module. When the information security management module receives data through the communication module, the data is decrypted first, integrity verification is carried out on the data after decryption, and if verification is passed, the data is sent out through the communication module; otherwise, the data is discarded.

In an embodiment, the identity authentication is realized by adopting an asymmetric key with a signature.

In an embodiment, the signature is realized by a pair of asymmetric keys which are trusted by the information security management module and the system, wherein the private key is used for signing the identities of the two communication parties, and the public key is used for verifying that the identities of the two communication parties are signed.

In an embodiment, the identity authentication is that both communication parties need to authenticate their own identities through a pair of asymmetric keys, and a task in charge of communication with the information security management module of the system is identified by a unique pair of asymmetric keys.

In an embodiment, the dynamic negotiation key is encrypted by adopting an Rivest-Shamir-Adleman (RSA) encryption algorithm. RSA is a public-key cryptosystem that is widely used for secure data transmission. The negotiated keys include a data encryption key and a data integrity check key.

In an embodiment, the data encryption method is a Triple Data Encryption Algorithm (3DES) encryption algorithm. The integrity check algorithm is a Hash-based Message Authentication Code (HMAC-MD5-128) algorithm. When data is output, integrity check calculation is carried out on the data, the calculated Message Authentication Code (MAC) value is added with the head of the value data message, then the data (including the MAC of the head) is encrypted by using a 3DES algorithm, the head information of a security layer is added after the data is encrypted, and then the data is sent to the next layer for processing.

In an embodiment the next layer refers to a transport layer in the Transmission Control Protocol/Internet Protocol (TCP/IP) model.

In an embodiment, when the receiving side finds an authentication error or a MAC decryption error, it is necessary to send a fatal error message to the transmitting side and close the connection.

The information security management module ensures the safety, reliability, and confidentiality of the communication between the system and the server through the identity authentication when the communication between the two communication parties starts the data encryption and the data integrity authentication in the communication process. The method is particularly suitable for an embedded platform which has less resources and is not connected with a Public Key Infrastructure (PKI) system and can ensure that the safety of the data on the server of the drug storage cannot be compromised by hacker attack under the condition of the Internet by ensuring the safety and reliability of the communication between the system and the server in the system for smart storage.

In an embodiment, a system hardening strategy is implemented to prevent at least one attack. An attack graph analysis may be used to help analyze network vulnerability. Once an attack graph of conditions and/or exploits (e.g., at least one goal condition, at least one initial condition, at least one exploit) is obtained, allowable actions that may harden the conditions may be obtained. Costs associated with the allowable actions may also be obtained. Recommended actions to harden the network with respect to one or more goal conditions may be determined.

Figure 6:
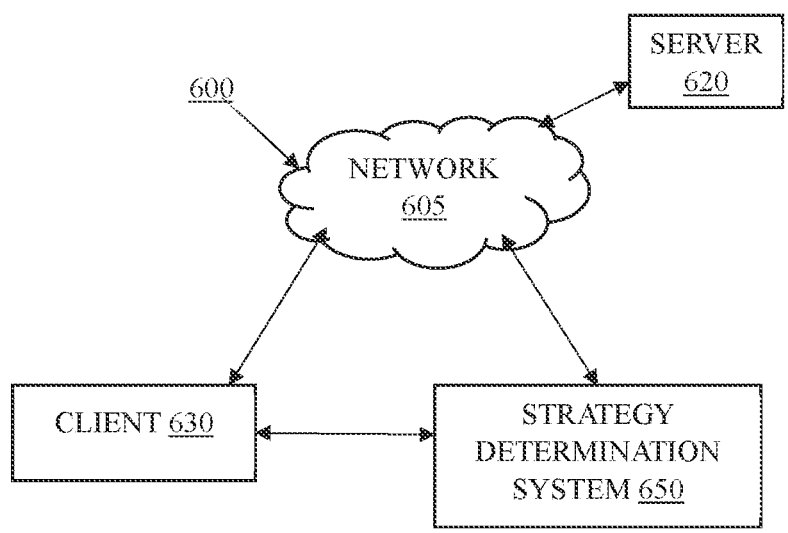
FIG. 6 is an example system where a system hardening strategy may be implemented according to an embodiment of the invention.

FIG. 6 is a system 600 according to an embodiment of the invention. In this example, the system 600 may comprise a network 605 (e.g., the Internet, an intranet) wherein one or more computers 620 (e.g., server, client) may communicate with one another. A strategy determination system 650 may communicate with the client and/or the server. The strategy determination system 650 may obtain an attack graph of conditions and/or exploits (e.g., using known techniques), obtain allowable actions that may remove one or more initial conditions to harden the network with respect to one or more goal conditions; obtain costs associated with the allowable actions, and determine recommended system hardening strategies to efficiently harden the network with respect to the goal condition(s), each system hardening strategy consisting of one or multiple allowable actions. As attackers may leverage complex interdependencies of network configurations and vulnerabilities to penetrate seemingly well-guarded networks, in an embodiment, the recommended actions may consider attacker exploits in isolation and/or in combination. Attack graphs may reveal such threats by enumerating potential paths that attackers can take to penetrate networks. This may help determine whether a given set of system hardening measures provides safety for given critical resources.

System hardening goal conditions may have a corresponding impact on removing paths in the attack graph. In addition, system hardening solutions that are optimal with respect to some notion of cost and/or time may be determined. Such system hardening solutions prevent the attack from succeeding, while minimizing the associated costs.

The strategy determination system 650 may comprise: a determine allowable actions module; an associate costs module; a determine recommended actions module; or an approximation module; or any combination thereof. In the strategy determination method, an attack graph comprising conditions and/or exploits may be obtained, allowable actions that remove one or more initial conditions may be obtained, costs associated with the allowable actions may be obtained, and recommended strategies comprising allowable actions may be determined based upon costs and/or time constraints.

Spyware is a type of malware that may be installed on computers and collects bits of information at a time about users without their knowledge. The presence of spyware is typically hidden from the user and may be difficult to detect. Spyware programs may collect various types of personal information, such as Internet surfing habits and sites that have been visited but may also interfere with user control of the computer in other ways, such as installing additional software and redirecting Web browser activity.

Figure 7:
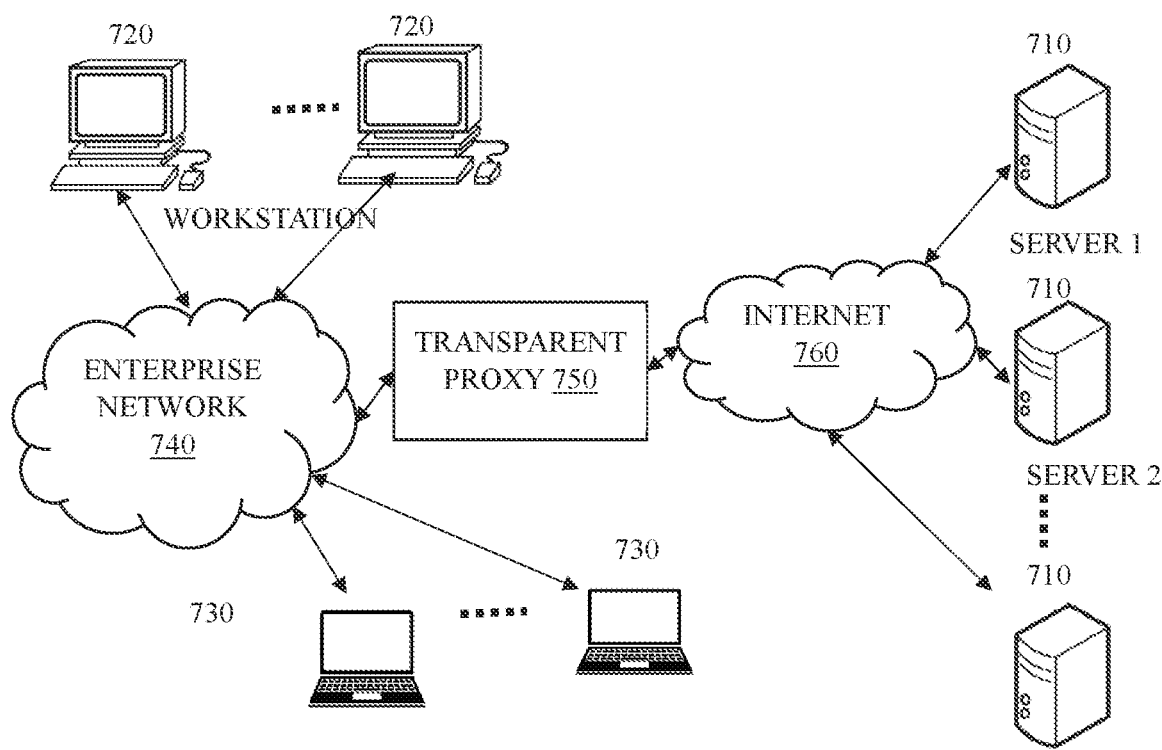
FIG. 7 shows an architecture of a network using a transparent proxy in an Enterprise network as per an aspect of an embodiment of the present invention for active malware detection.

Passive detection may identify a fraction of the malware that is collected in an enterprise network but may not identify all of them. Embodiments of the present invention utilize active detection mechanism(s). The active detection mechanism(s) may also be called Active Content Challenges and may be implemented using a transparent proxy. FIG. 7 shows the architecture of a network using an embodiment of the transparent proxy 750 in an Enterprise network 740 including workstations 720 and laptops 730. The architecture may be fully transparent and may not require any application or network modifications both for client applications and servers and may accommodate various protocols including HTTP, encrypted HTTP (HTTPS) and Voice over IP (VOIP) protocols. The transparent proxy 750 may mediate all traffic both encrypted and unencrypted when an application initiates a communication with a server 710 connected to Internet 760 outside the enterprise. Communication may pass through the firewall while being examined and analyzed by the transparent proxy 750. According to an embodiment, a transparent proxy may be in a laptop or workstation. The transparent proxy may mediate all traffic both encrypted and unencrypted when an application initiates a communication with a remote server connected to the internet.

The transparent proxy 750 may intercept outbound requests and issue Active Content Challenges to the requesting application. The principle is similar to Turing puzzles and Captchas, however, rather than trying to distinguish a human from software, the objective is to distinguish legitimate software from malware. Thus, unlike existing mechanisms that demand end-users to be involved in the identification process by solving a puzzle, the approach in this embodiment requires no user involvement or application modification. The transparent proxy for malware detection may include a monitor module, a protocol determination module, a challenge generation module, a response determination module, and a data control module. The transparent proxy may include interfaces for receiving and transmitting applications traffic and remote server traffic. The transparent proxy may be located on a network edge or on a laptop or workstation and may examine outgoing traffic. In general, the approach frustrates the communication of the malware by injecting traffic that the malware is incapable of parsing and generating a valid response contrary to the legitimate application.

In an embodiment, a secure virtual browsing environment is provided which includes creating a virtual browsing environment with a virtualized operating system sharing an operating system kernel of a supporting operating system and executing the browser application within the virtual browsing environment. Another embodiment includes receiving a website selection within a browser application, determining if the website selection corresponds to a secure bookmark, and creating a second virtual browsing environment and executing the browser application within the second virtual browsing environment to access the website selection when the website selection corresponds to a website specified as a secure bookmark. Another embodiment includes monitoring operation of the operating system within the at least one virtual browsing environment, determining when the operation of the operating system includes potential malicious activity, and terminating the virtual browsing environment when the operation includes potential malicious activity.

Figure 8A:
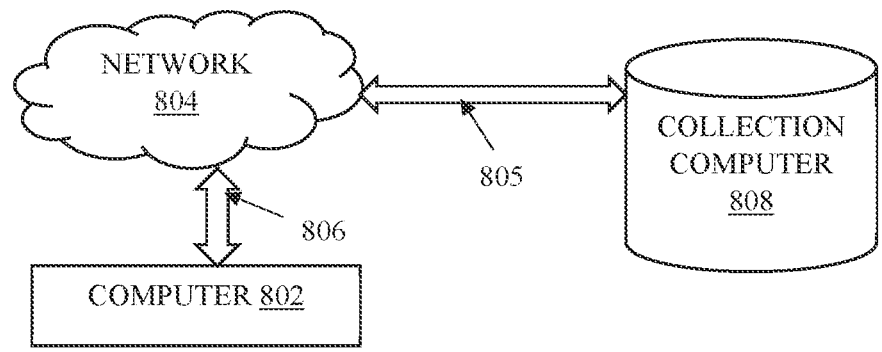
FIG. 8A illustrates a system for providing a virtual browsing environment according to an aspect of an embodiment of the invention.

FIG. 8A illustrates a system 800 for providing a virtual browsing environment according to one embodiment of the invention. As described below, embodiments of the system 800 may provide a virtual browsing environment for executing a browser application on a computer. By executing the browser application within a separate virtual browsing environment, other applications, data, and modules of the computer may be protected from any malicious activity associated with the execution of the browser application. In addition, because in some embodiments only the browser application may be executed within the virtual browsing environment, malicious activity associated with the execution of the browser application may be easily detected. The system 800 may include at least one computer 802, at least one network 804, and at least one collection computer ("CC") 808 and other components. The computer 802 and the network 804 may be connected by a connection 806, and the network 804 and the collection computer 808 may be connected by a connection 805. The collection computer 808 may receive data from the network 804 over the connection 805. In some embodiments, the collection computer 808 may also send data to the network 804 or one or more computers or networks. The collection computer 808 may also include hardware, such as one or more memory modules, one or more processors, and one or more input/output modules. In addition, the collection computer 808 may include an operating system to manage the hardware. In some embodiments, the collection computer 808 may also include a database that stores data received from the network 804. The data included in the database may be stored in the collection computer's 808 one or more memory modules, and the data may be managed by a database management application.

Figure 8B:
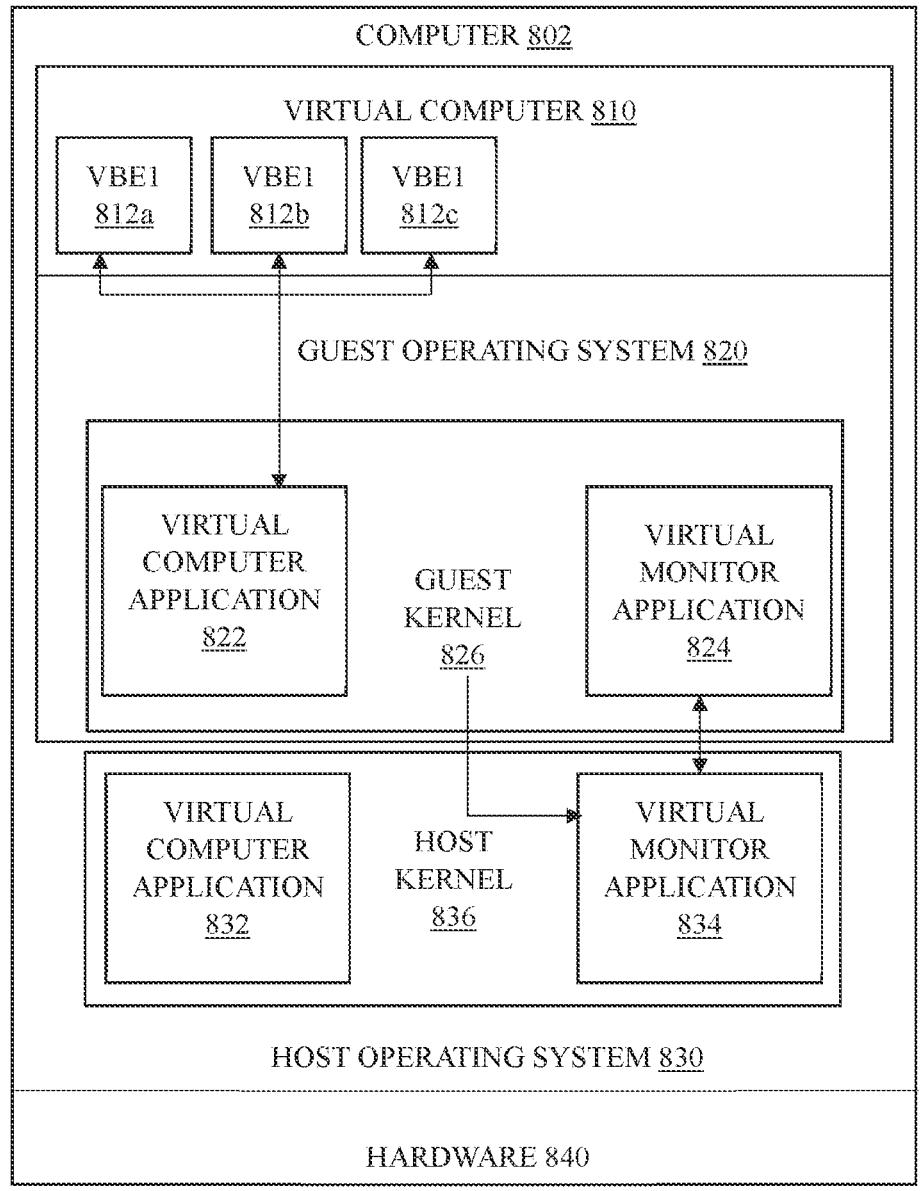
FIG. 8B illustrates a computer included in the system of FIG. 13A, according to an embodiment of the invention.

FIG. 8B illustrates the computer 802 of FIG. 8A which includes a host operating system 830 that provides an interface between the hardware 840 and a user operating the computer 802. The host operating system 830 may be stored in the one or more memory modules and may be executed on the one or more processors included in the hardware 840. The host operating system 830 may include at least one host kernel 836. The host kernel 836 may manage the communication between the hardware 840 and applications executed by the hardware 840. The host kernel 836 may use the virtual control application (VCA) 834 to create and manage a virtual computer. Accordingly, the VCA 834 may provide virtualization functionality. The host kernel 836 may also include a shared preference directory 832, which may store preferences for an application, such as a browser application. It should be understood that the one or more memory modules included in the hardware 840 may store other applications besides those explicitly shown in FIG. 8B. In addition, the functionality provided by the applications stored in the one or more memory modules may be combined and distributed in various configurations.

In operation, as shown in FIG. 8B, the host kernel 836 may execute the VCA 834 to create a virtual computer 810. The virtual computer 810 may include its own guest host operating system 820 with a guest kernel 826. The guest operating system 820 and guest kernel 826 may operate similar to the host operating system 830 and host kernel 836. This type of virtualization where a generally complete copy of an operating system is provided within a virtual computer is generally referred to as "full virtualization." Outside of the virtual computer 810, the host operating system 830 may continue to interact and manage the hardware 840, while the guest operating system 820 also may interact and manage the hardware 840. Therefore, the virtual computer 810 may create a second, isolated computing environment within the computer 802. Each computing environment may execute different applications, access data from different locations in a memory module or from different memory modules, provide different operating systems, or combinations thereof. Creating the virtual computer 810 may provide isolation between computing performed within the virtual computer 810 and computing performed outside the virtual computer 810 through the host operating system 830. For example, the virtual computer 810 may be unaware of any computing performed outside of the virtual computer 810. Accordingly, an application executed within the virtual computer 810 generally cannot access an application executed outside the virtual computer 810.

As shown in FIG. 8B, the guest kernel 826 may include a virtual computer control application ("VCCA") 822 and a virtual computer monitor application ("VCMA") 824. The VCCA 822 may manage the operation of the virtual computer 1310. For example, as shown in FIG. 8B, the VCCA 822 may create one or more virtual browsing environments ("VBE") 812 (e.g., VBE 1 812 a, VBE 2 812 b, and VBE 3 812 c). Once created, the VCMA 824 may monitor the operation of each VBE 812 and may report each VBE's operation to the VCA 834. To create a VBE 812, the VCCA 822 may use one or more virtualization modules or applications, such as OpenVZ, UnionFS patches, Solaris Zones, BSD Jail, or combinations thereof.

It is known that internet-enabled applications run side-by-side with all other desktop and system software with the privileges of the user. As a result, when a compromise occurs through the Internet, the entire system can be compromised by a single vulnerability in an Internet-enabled software such as a Web browser or an email client. By simply browsing to a Web page, a user can compromise their system, sometimes irreversibly.

In an embodiment, the system works by launching a virtual machine for each Internet-enabled or untrusted application that is started. The virtual machine provides a pristine guest operating system (OS) for the Internet-enabled or untrusted application that is launched. This operating system may be an operating system unmodified from the original version delivered by the manufacturer or another version suitably configured for the task of running intended applications. The virtual machine and its guest operating system may be temporally limited to exist only for the duration of the session of the application. When the user exits the application, the virtual machine can be destroyed. For the duration of the session, the virtual machine provides an isolated environment from the host machine from which it is launched. The virtual machine provides a level of isolation from the host machine that is the equivalent to running a physically separate machine from the host machine. Any attacks that occur on the machine via an Internet connection can compromise only the virtual machine that is started up for that session. When the session is terminated, so is the virtual machine and the compromise. With each new session, a pristine new virtual machine is started up, meaning that any malicious software that was downloaded or planted during a prior session is no longer present. The underlying host operating system does not need to maintain an Internet connection. As a result, Internet-based attacks have a very limited ability to compromise the host operating system.

Figure 9:
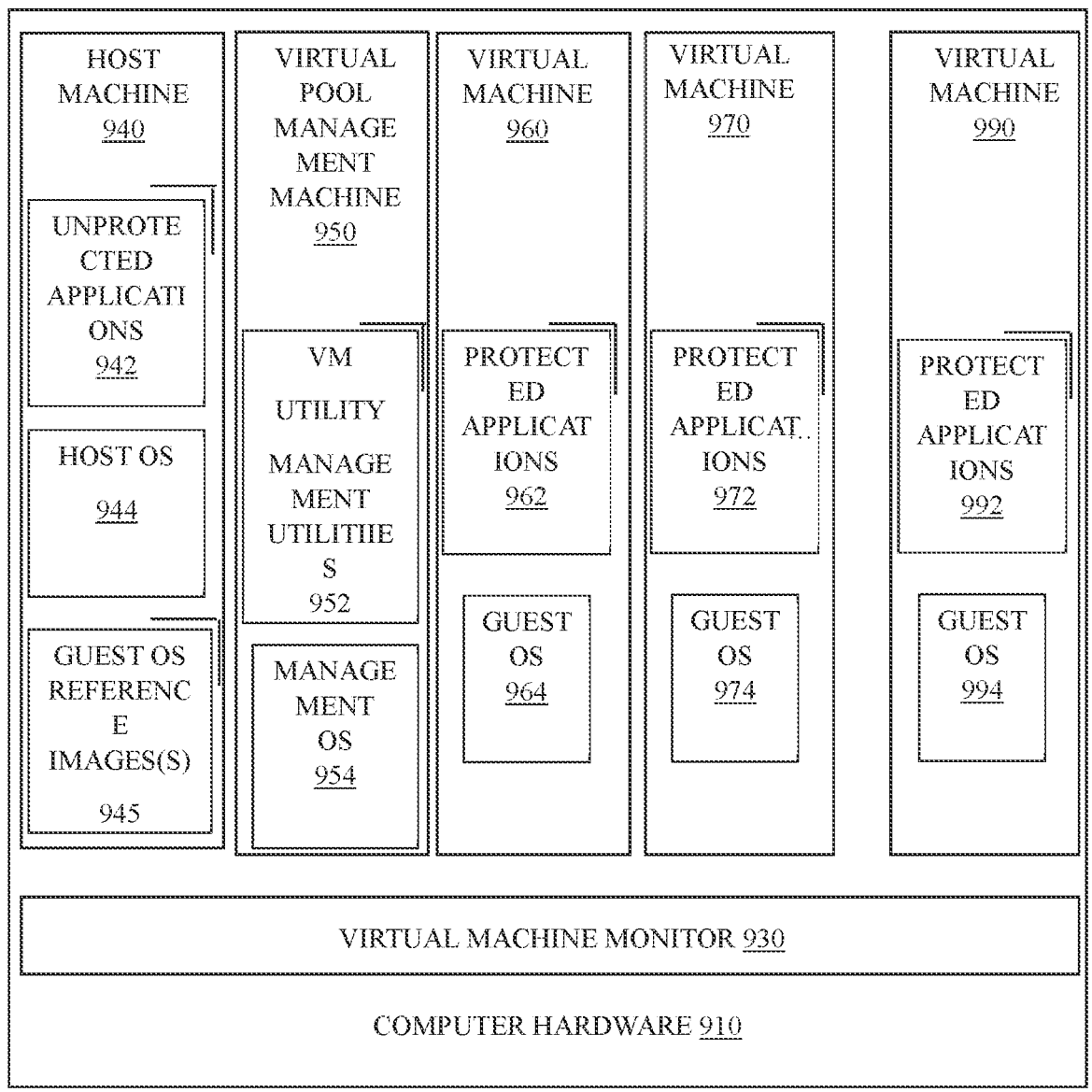
FIG. 9 is a block diagram of a virtual machine architecture of an aspect of an embodiment of the present invention to prevent malicious software attack.

According to an embodiment, an architecture shown in FIG. 9 uses the standard virtual machine architecture with the Virtual Machine Monitor (VMM) 930 running on the computer hardware 910, and host operating systems (944, 954, 964, 974, and 994) running on top of the VMM 930. A host operating system (OS) 944 is defined as the default machine the user normally uses and is the machine whose desktop is presented to the user. Guest OSs (964, 974 and 994) are created by request when a protected application (962, 972 and 992) is launched, or created in advance to enable higher performance when launching protected applications (962, 972 and 992) into pre-instantiated guest OSs (964, 974 and 994). A Management VM 950 may be bootstrapped along with the Host OS 944 and a reference guest OS image 945 that is used for clones of the guest OS reference image 945. The Management VM 950 is used for command, control, and lifecycle maintenance of the guest OSs (964, 974 and 994) based on the instructions from the host OS 944. The number of guest OSs instantiated may be dependent on the number of protected applications launched and the performance limits of the underlying hardware. The VMM 930 and VM 950 should support live capture of the full system state in a file for subsequent replay. This file is called a "snapshot" of system state.

The host operating system 944 may be configured for higher security so that it is unable to make Internet connections itself. The guest operating systems (964, 974 and 994) may be free to make direct Internet connections; however, they should be restricted from freely accessing the host operating system 944 by the virtual machine monitor 930 that runs in its own hardware protection domain which provides hardware-equivalent strong isolation between the virtual machine and its host operating system. The guest operating systems (964, 974 and 994), which are pristine builds of the OS, should also be "root secure", which means that even if one of the guest operating systems (964, 974 and 994) is compromised to a root user level or the kernel itself is compromised, the host operating system 944 itself should not be compromised by the compromised guest operating system. Once a guest operating system is destroyed (upon closure of the protected application that started the guest OS), the compromise is now removed from the system.

As mentioned earlier, a reference guest OS image 945 may be booted along with the host OS 944. A snapshot of the reference guest OS image 945 may be taken, then used to derive subsequent VM images by cloning it, i.e., creating a replica image of the reference guest OS. When a new untrusted application is to be started, a dispatch instruction is sent from the Host OS to the Virtual Pool Management Machine 950, which then creates a VM for the application using the reference guest OS image, if the VM has not already been created. By cloning and pre-booting reference images, the response time for instantiating the application should be on par or even faster than the usual response time for starting a new application for users.

As described, FIG. 9 shows an embodiment of the present invention where virtual machines (VM) monitor 930 runs directly on computer hardware 910. In this embodiment, every host machine (940, 950, 960, 970 and 990) is essentially a guest machine to the computer hardware. In this setup, the unprotected host applications 942 run on the host machine 940 natively and the host operating system 944 runs these unprotected host applications 942. In contrast, the guest virtual machines 960, 970 and 990 run protected applications (962, 972, and 992 respectively) that may talk to a network under guest operating systems (964, 974 and 994 respectively).

The guest operating systems 964, 974, and 994 are each cloned from one of the guest operating system images(s) 945, and the images 945 should be pristine snapshots of a running operating system. To increase speed, the snapshots may also include running applications. For example, an image 945 of an operating system for an email virtual machine can include a copy of an email application running under the operating system.

The virtual pool management machine 950 runs a series of virtual machine management utilities 952 under a management operating system 954. These utilities 952 include functions that: create, destroy, put to sleep, and wake up virtual machines. The utilities also maintain a list that matches applications to virtual machines. In other embodiments, these same functions may be performed by pool management utilities running on a host machine.

Figure 10:
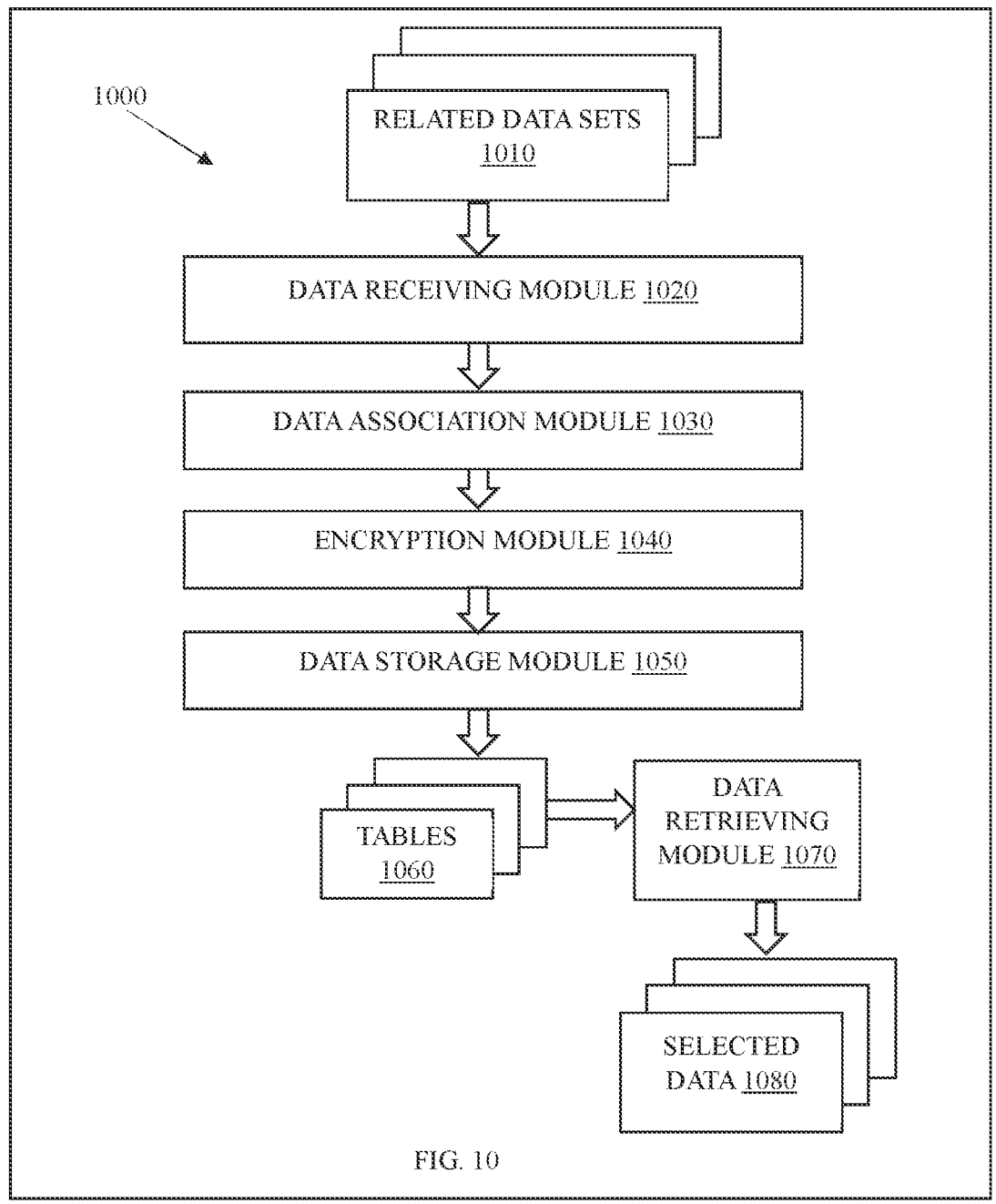
FIG. 10 is a block diagram for securing sensitive data associations for related data values of an aspect of an embodiment of the present invention.

In an embodiment, sensitive data associations for related data values are protected. FIG. 10 is a block diagram of a system 1000 for protecting sensitive data associations according to an aspect of an embodiment of the present invention. The block diagram shows a multitude of modules. As shown, the system includes a data receiving module 1020 configured to receive a set(s) of related data values 1010. The set(s) of related data values 1010 preferably include at least a first data value and a second data value. The system normally operates against rule(s) that indicate which data value associations need to be kept secret. In the absence of such a rule, a default rule may be used such as the association of the first data value and the second data value needs to be kept secret.

A data association module 1030 may be configured to associate the first data value to a first data field; and the second data value to a second data field. An encryption module 1040 may then create first encrypted data by encrypting the first data value using a first encryption key; and create second encrypted data by encrypting the second data value using a second encryption key. A data storage module 1050 is configured to store: the first data value in a first data table 1060; the second data value in a second data table 1060; the first encrypted data in the second table 1060; and the second encrypted data in the first table 1060.

A data retrieving module(s) 1070 may be used to retrieve: the first data value by decrypting the first encrypted data using a first decryption key and/or the second data value by decrypting the second encrypted data using a second decryption key. As with the method embodiments, there are many possibilities for the encryption and decryption keys. The encryption key and the decryption key may be the same symmetric key. The encryption keys may be different or the same. Similarly, the decryption keys may be the same or different. The choice of keys should be made carefully to ensure that the data relationships in the rule(s) be kept secret. In some embodiments, the rule may be received from an external source. In the absence of an external rule, an internal rule or a default rule may be used.

In an embodiment, there is a tool for storing data records in a data store that is scalable and that allows a user to define their encryption and relieves a user from the task of managing keys used for data security. In an embodiment, application data and associated encryption key(s) are stored on at least k+1 remote servers using Linear hashing (LH*) addressing. At least k+1 buckets are created on separate remote servers. At least k+1 key shares are generated for each of at least one encryption key. Each encryption key has a unique key number. Each key share is stored in a different key share record. Each of the key share records is stored in a different bucket using LH* addressing. Encrypted application data is generated by encrypting the application data with the encryption key(s). The encrypted application data is stored in encrypted data record(s). Each of the encrypted data records is stored in a different bucket among the buckets using LH* addressing.

Figure 11:
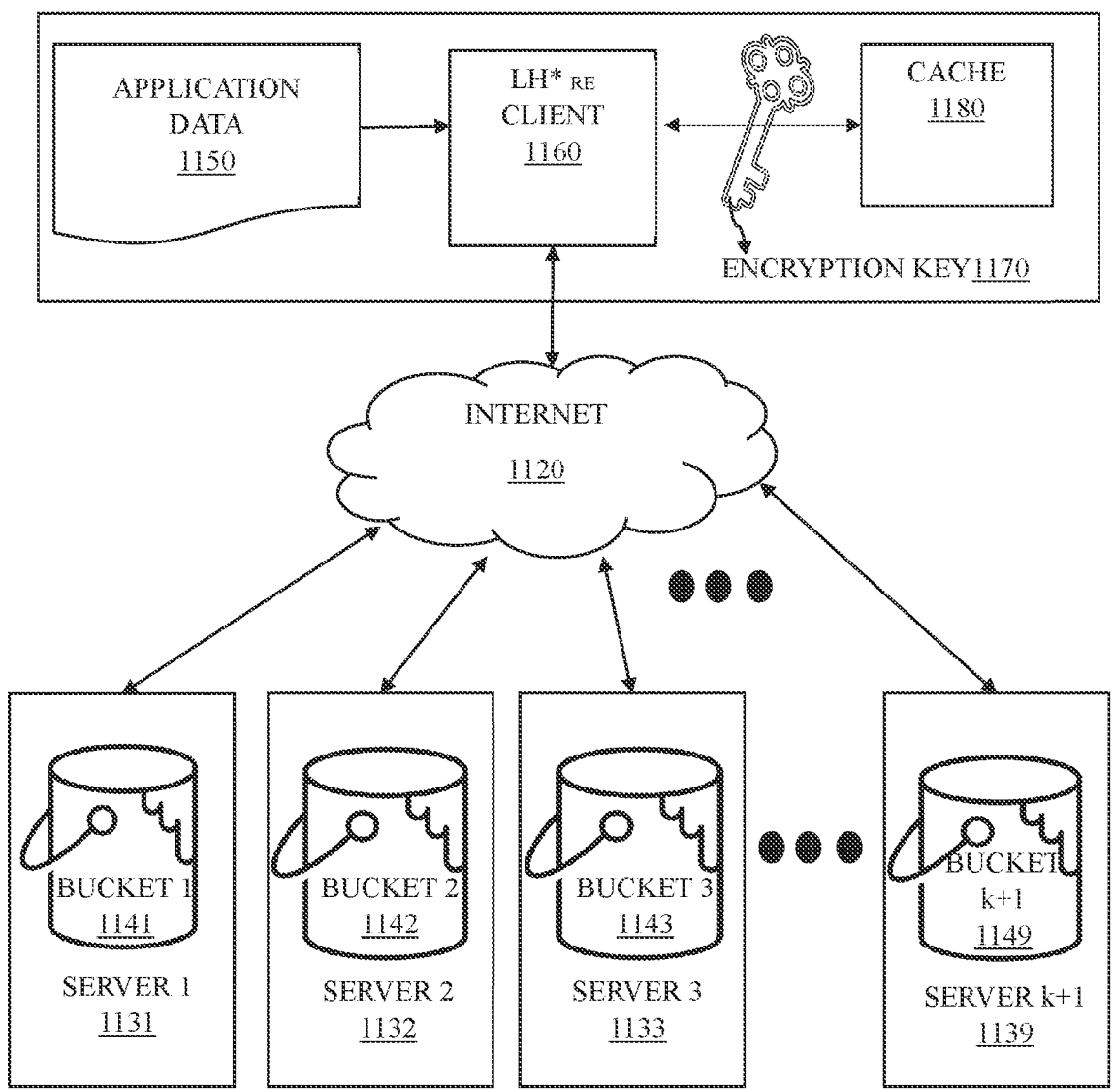
FIG. 11 is a system block diagram showing an example client interacting with k+1 servers that allows a user to define their encryption and relieves a user from the task of managing keys used for data security, as per an aspect of an embodiment of the present invention.

FIG. 11 is a system block diagram showing an example client 1110 interacting with k+1 remote servers (1131, 1132, 1133, . . . 1139) as per an aspect of an embodiment of the present invention. In these embodiments, one or more of clients (1110, 1111, ... 1119) may have an LH*RE client 1110 configured to store a version of application data 1150 encrypted with an encryption key 1170 on remote servers (1131, 1132, 1133, ... 1139). The remote servers (1131, 1132, 1133, ... 1139) will likely be specialized servers configured to communicate with many client systems (1110, 1111 ... 1119) and manage data buckets (1141, 1142, 1143, ... 1149). The remote servers (1131, 1132, 1133, ... 1139) may be geographically diverse. Some of the remote servers (1131, 1132, 1133, ... 1139) may also be under the control of various organizations. In this way, the stored data may become harder for a third party to locate and retrieve all of the stored application data 1150 and key(s) 1170 from the data. Embodiments of the LH*RE client 1160 may be implemented as a computer readable storage medium containing a series of instructions that when executed by one or more processors on clients (1110, 1111, ... 1119), causes the one or more processors to store application data 1150 on at least k+1 remote servers (1131, 1132, 1133, ... 1139). In these embodiments, k is a freely set parameter of the system.

Figure 12:
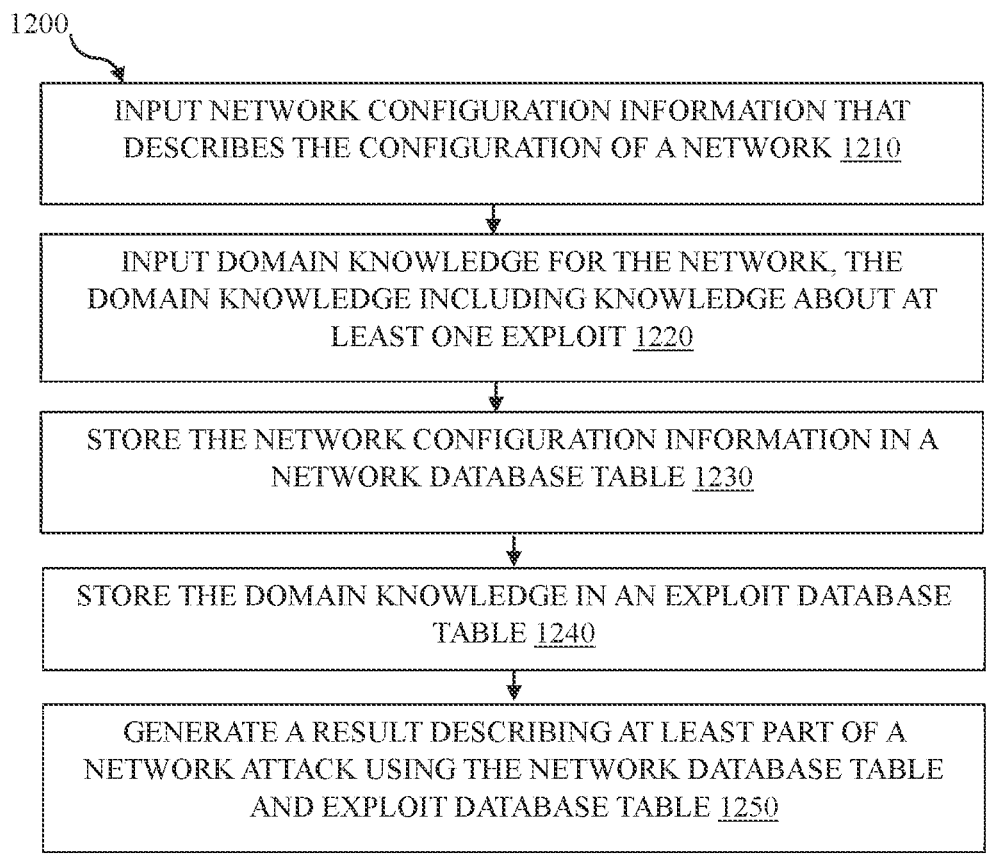
FIG. 12 is a flow diagram describing a method for determining at least part of a network attack according to an embodiment of the present invention.

Attack graphs depict ways in which an adversary exploits system vulnerabilities in a network such as a computer network. Attack graphs may be important in defending against well-orchestrated network intrusions. FIG. 12 is a flow diagram of an aspect of an embodiment where the network configuration information input module is preferably configured to input network configuration information that describes the configuration of a network in 1210. The domain knowledge input module is preferably configured to input domain knowledge for the network in 1220. Domain knowledge may include knowledge about various exploits in the network. The network configuration information storage module is preferably configured to store network configuration information in at least one network database table in 1230. Similarly, the domain knowledge storage module is preferably configured to store the domain knowledge in at least one exploit database table 1240. The result generation module is preferably configured to generate a result using the network database table and exploit database table in 1250. The result may be generated in many ways.

In an embodiment, an Intrusion Detection System (IDS) is deployed on the system. An IDS is software and/or hardware designed to detect unwanted attempts at accessing, manipulating, and/or disabling computer systems, mainly through a network, such as the Internet. An intrusion detection system is used to detect malicious behaviors that can compromise the security of networked computer systems. An IDS may include Sensor(s) that are deployed at strategic locations in the network, which monitor traffic at the sensor location and generate security events upon detection of malicious behaviors; A central engine that records events (e.g., in a database) logged by the sensors; and Console(s) to monitor events and control the sensors. In some IDS implementations, all three components are combined in a single device or appliance. In a true distributed system, numerous sensors are deployed at various points in the network, which communicate over secure channels to the central engine. Multiple consoles may then interact with the central engine. In network-based intrusion detection systems (NIDS), sensors are located at monitoring points in a network. Traditionally, sensors may be placed at network borders or in a network demilitarized zone (DMZ), with the assumption that attacks are launched from outside the network to be defended. The sensor monitors network traffic at its point of deployment and analyzes the traffic content for patterns of malicious behavior.

Embodiments of the present invention locate the placement of intrusion detection system (IDS) sensors and prioritize IDS alerts using attack graph analysis. One embodiment predicts multiple ways of penetrating a network to reach critical assets. The set of such paths through the network constitutes an attack graph, which may be aggregated according to underlying network regularities, reducing the complexity of analysis. By knowing the paths of vulnerability through our networks, one may reduce the impact of attacks. IDS sensors may be placed to cover the attack graph, using a minimal number of sensors. This should minimize the cost of sensors, including effort of deploying, configuring, and maintaining them, while maintaining complete coverage of potential attack paths. An embodiment addresses the sensor placement as an instance of the non-deterministic polynomial-time (NP) hard minimal set cover problem using an efficient greedy algorithm. Once sensors are deployed and alerts are raised, a predictive attack graph may be used to prioritize alerts based on attack graph distance to critical assets.

Figure 13:
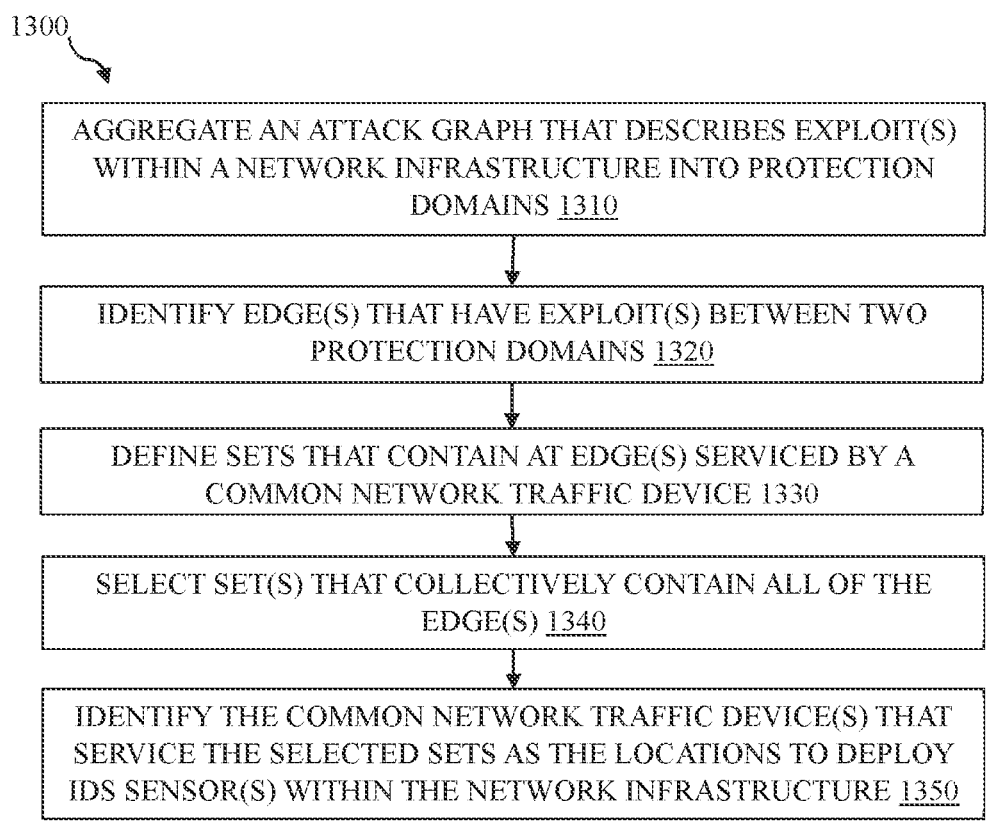
FIG. 13 depicts a flow diagram for a computer readable storage medium demonstrating instructions that cause the processor to perform a method for identifying locations to deploy intrusion detection system (IDS) Sensors within a network infrastructure, as per an aspect of an embodiment of the present invention.

An embodiment of the present invention, as exemplified in FIG. 13, is a computer readable storage medium that contains instructions that when executed by at least one processor, causes the processor(s) to perform a method 1300 for identifying locations to deploy IDS sensor(s) within a network infrastructure. The method 1300 for identifying locations to deploy IDS sensor(s) within a network may comprise aggregating an attack graph that describes exploit(s) within a network infrastructure into protection domains 1310. The attack graph may be configured to describe exploit(s) in at least a part of the network infrastructure. Further, the embodiment may include identifying edge(s) that have exploit(s) between two protection domains 1320, defining sets that contain edge(s) serviced by a common network traffic device 1330, selecting set(s) that collectively contain all of the edge(s) 1340, and identifying the common network traffic device(s) that service the selected sets as the locations to deploy IDS sensor(s) within the network infrastructure 1350.

In an embodiment of the present invention, the selecting set(s) that collectively contain all of the edge(s) 1340 may further include selecting set(s) that cover critical path(s) through the network infrastructure that lead to a critical asset. The set selection method 1340 may further include selecting set(s) that cover critical path(s) through the network infrastructure that starts at an assumed threat source. Further variations of this embodiment may allow the set selection method 1340 to include selecting a minimal number of sensors necessary to cover critical path(s) through the network infrastructure. The set selection method 1340 may also further include utilizing a greedy algorithm. The greedy algorithm favors large sets that contain edge(s) that are infrequently used. Frequency is the number of times an edge appears across all sets.

In an embodiment of the present invention, the method 1300 for identifying locations to deploy on IDS sensor(s) within a network may further include prioritizing alerts from IDS sensors deployed within the network infrastructure using at least one attack graph distance to at least one critical asset. Attack graph distance may be measured in multiple ways such as: 1) the number of edges that are traversed to reach critical assets; 2) the number of protection domains crossed; and 3) the number of network traffic devices.

INCORPORATION BY REFERENCE

All references, including granted patents and patent application publications, referred to herein are incorporated herein by reference in their entirety.
U.S. Publication Number US20210249112A1 titled "Integrated device and system for drug dispensing";
U.S. Publication Number US20210398635A1 titled "Medication compliance device";
U.S. Publication Number U.S. Ser. No. 11/100,741B2 titled "Secure inventory access and control mechanism";
U.S. Publication Number US20210343404A1 titled "Health management system";
U.S. Publication Number US20160022542A1 titled "Home medication manager";
U.S. Publication Number U.S. Ser. No. 10/709,643B2 titled "Tamper-proof pill dispensing system and methods of use";
U.S. Pat. No. 9,203,861 titled "Methods and systems for determining hardening strategies";
U.S. Pat. No. 9,436,822 titled "Virtual browsing environment";
U.S. Pat. No. 10,956,184 titled "Malware detector";
U.S. Pat. No. 9,846,588 titled "on demand disposable virtual work system";
U.S. Pat. No. 8,082,452 titled "Protecting sensitive data associations";
U.S. Publication 20100054481 titled "Scalable distributed data structure with recoverable encryption";
U.S. Pat. No. 8,566,269 titled "Interactive analysis of attack graphs using relational queries";
U.S. Publication 20100058456 titled "IDS sensor placement using attack graphs".

What is claimed is:

1. A system for drug dispensing, comprising:
a drug dispenser;
at least one authentication sensor;
at least one bio-feedback monitoring device;
a prescription scanner;
a database comprising records of patients and records of practitioners;
a processor; and
a memory;
wherein the processor is communicatively coupled with the memory, and the processor is operable to:
 receive an identity credential of a user;
 perform a first level authentication of information of the user based on the identity credential;
 monitor at least one vital of the user via the bio-feedback monitoring device;
 receive a prescription via the prescription scanner;
 perform a second level authentication of the at least one vital of the user, the prescription and an identity of a practitioner received via the prescription;
 check and authenticate dispensing of a drug with an inventory of the drug according to the information of the user; and
 dispense the drug through the drug dispenser when both the first level authentication and the second level authentication are successful; and wherein the system is configured to lock the drug dispenser if at least one of the first level authentication and the second level authentication fails, thereby preventing the drug dispensing until successful authentication is achieved.

2. The system of claim 1, wherein the identity credential comprises at least one of a unique identity of the user, and biometric information of the user.

3. The system of claim 2, wherein the first level authentication comprises matching the identity credential against the records of patients and the records of practitioners.

4. The system of claim 2, wherein the second level authentication comprises matching the biometric information against the records of practitioners and the records of patients.

5. The system of claim 2, wherein the unique identity of the user comprises at least one of a unique identification number, an RFID tag, a password, a barcode, and a Quick response QR code.

6. The system of claim 2, wherein the biometric information comprises at least one of a fingerprint, an eyeblink, a retina scan, an iris scan, an eye scan, and a facial image scan.

7. The system of claim 1, wherein the at least one vital of the user comprises at least one of a pupil dilation of the user, a breathing rate of the user, a heart rate of the user and a blood pressure of the user.

8. The system of claim 7, wherein the at least one vital received by the system is monitored by comparing it with a range of values of the at least one vital of the user in the database; and
wherein the system comprises an alarm to generate an alert through the alarm to notify the practitioner if the at least one vital of the user monitored is abnormal; and wherein the at least one vital is abnormal if the at least one vital received by the system is not within the range of values of the at least one vital of the user in the database.

9. The system of claim 1, wherein the processor interacts with the database to check a drug name, a last dispensing time, a dosage time, a quantity of the drug delivered to the user in a day, quantity of the drug accessed by the user in the day before dispensing the drug to the user.

10. The system of claim 1, wherein an output of the bio-feedback monitoring device controls a quantity of the drug dispensed from the drug dispenser.

11. A method comprising:
receiving an identity credential of a user, the identity credential comprising at least one of a unique identity of the user, and biometric information of the user;
performing a first level authentication of information of the user based on the identity credential;
monitoring at least one vital of the user via a bio-feedback monitoring device;
receiving a prescription;
performing a second level authentication of the at least one vital of the user, the prescription and an identity of a practitioner received via the prescription;
checking and authenticating dispensing of a drug with an inventory of the drug according to the information of the user;
dispensing the drug through a drug dispenser when both the first level authentication and the second level authentication are successful; and
locking the drug dispenser if at least one of the first level authentication and the second level authentication fails, thereby preventing the dispensing until successful authentication is achieved.

12. The method of claim 11, wherein an output of the bio-feedback monitoring device controls a quantity of the drug dispensed from the drug dispenser.

13. The method of claim 11 further comprising updating the inventory after dispensing of the drug.

14. The method of claim 13 further comprising maintaining a log of record of dispensing of the drug; and maintaining a ledger of record of dispensing of the drug using blockchain technology.

15. The method of claim 11, wherein the method further comprises registering the identity credential in a database comprising records of patients and records of practitioners.

16. The method of claim 15, wherein the unique identity comprises at least one of a unique identification number, an RFID tag, a password, a barcode, and a Quick response QR code.

17. The method of claim 15, wherein the biometric information comprises at least one of a fingerprint, an eyeblink, a retina scan, an iris scan, an eye scan, and a facial image scan.

18. The method of claim 11, further comprising unlocking the drug dispenser after the first level authentication of an authorized owner of the drug dispenser.

19. A system for drug dispensing, comprising:
a drug dispenser;
at least one authentication sensor;
at least one bio-feedback monitoring device;
a database comprising records of patients and records of practitioners;
a processor; and
a memory;
wherein the processor is communicatively coupled with the memory, and the processor is operable to:
receive an identity credential of a user;
perform a first level authentication of information of the user based on the identity credential;
monitor at least one vital of the user via the bio-feedback monitoring device;
receive a prescription;
perform a second level authentication of the at least one vital of the user, the prescription and an identity of a practitioner received via the prescription;
check and authenticate dispensing of a drug with an inventory of the drug according to the information of the user;
dispense the drug through the drug dispenser when both the first level authentication and the second level authentication are successful; and
lock the drug dispenser if at least one of the first level authentication and the second level authentication fails, thereby preventing the drug dispensing until successful authentication is achieved.

20. The system of claim 19, herein the prescription is received via one of a digital medium, a prescription scanner, and as a blockchain token; and wherein the digital medium comprises a message, and an email.

* * * * *